US008725547B2

(12) United States Patent
Fuhrmann et al.

(10) Patent No.: US 8,725,547 B2
(45) Date of Patent: May 13, 2014

(54) UTILIZATION INDICATING SCHEDULE SCANNER

(75) Inventors: David E. Fuhrmann, Madison, WI (US); Steven J. Larsen, Cross Plains, WI (US); Keith A. Foss, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 2058 days.

(21) Appl. No.: 11/134,642

(22) Filed: May 20, 2005

(65) Prior Publication Data

US 2006/0047553 A1    Mar. 2, 2006

Related U.S. Application Data

(60) Provisional application No. 60/604,154, filed on Aug. 24, 2004.

(51) Int. Cl.
*G06Q 10/00* (2012.01)
(52) U.S. Cl.
USPC .............................. 705/7.15; 705/7.24; 705/2
(58) Field of Classification Search
CPC ................ G06Q 10/063114; G06Q 10/06314
USPC ........................................... 705/7.15, 7.24, 2
See application file for complete search history.

(56) References Cited

U.S. PATENT DOCUMENTS

| | | | |
|---|---|---|---|
| 4,591,974 A | 5/1986 | Dornbush et al. | |
| 4,667,292 A | 5/1987 | Mohlenbrock et al. | |
| 4,839,806 A | 6/1989 | Goldfischer et al. | |
| 4,893,270 A | 1/1990 | Beck et al. | |
| 4,937,743 A * | 6/1990 | Rassman et al. | 705/7.22 |
| 4,962,475 A | 10/1990 | Hernandez et al. | |

(Continued)

FOREIGN PATENT DOCUMENTS

| | | |
|---|---|---|
| WO | WO 96/27163 | 9/1996 |
| WO | WO 98/13783 | 4/1998 |

(Continued)

OTHER PUBLICATIONS

Wisconsin Organizational Resource Consultants, "Consulting and Software for Healthcare and Your Business" (Aug. 6, 2004), accessed from: http://web.archive.org/web/20040806170323/www.healthworcs.com/orworcs.html.*

(Continued)

*Primary Examiner* — Beth V Boswell
*Assistant Examiner* — Tiphany Dickerson
(74) *Attorney, Agent, or Firm* — Quarles & Brady LLP

(57) ABSTRACT

A method and apparatus for use with a processor, a database and an interface including a display screen, the database including schedule information associated with utilization of time for at least one medical resource that may be scheduled for use over a period including several sub-periods, the method for aiding a scheduler responsible for scheduling the resource to optimally schedule new requests for the resource's time, the method comprising the steps of identifying a utilization value for at least one schedule sub-period for the at least one resource wherein the utilization value indicates current use of time for the at least one sub-period for the at least one resource, identifying an optimization indicator at least in part as a function of the utilization value for the at least one sub-period and presenting the optimization indicator via the display.

27 Claims, 9 Drawing Sheets

(56) References Cited

U.S. PATENT DOCUMENTS

| | | | |
|---|---|---|---|
| 5,072,383 A | 12/1991 | Brimm et al. | |
| 5,072,412 A | 12/1991 | Henderson, Jr. et al. | |
| 5,072,838 A | 12/1991 | Price, Jr. et al. | |
| 5,077,666 A | 12/1991 | Brimm et al. | |
| 5,088,981 A | 2/1992 | Howson et al. | |
| 5,101,476 A | 3/1992 | Kukla | |
| 5,253,362 A | 10/1993 | Nolan et al. | |
| 5,301,105 A | 4/1994 | Cummings, Jr. | |
| 5,319,543 A | 6/1994 | Wilhelm | |
| 5,325,478 A | 6/1994 | Shelton et al. | |
| 5,361,202 A | 11/1994 | Doue | |
| 5,428,778 A | 6/1995 | Brookes | |
| 5,546,580 A | 8/1996 | Seliger et al. | |
| 5,557,515 A | 9/1996 | Abbruzzese et al. | |
| 5,574,828 A | 11/1996 | Hayward et al. | |
| 5,596,752 A | 1/1997 | Knudsen et al. | |
| 5,603,026 A | 2/1997 | Demers et al. | |
| 5,640,595 A * | 6/1997 | Baugher et al. | 710/10 |
| 5,692,125 A | 11/1997 | Schloss et al. | |
| 5,724,584 A | 3/1998 | Peters et al. | |
| 5,748,907 A | 5/1998 | Crane | |
| 5,751,958 A | 5/1998 | Zweben et al. | |
| 5,760,704 A | 6/1998 | Barton et al. | |
| 5,772,585 A | 6/1998 | Lavin et al. | |
| 5,778,346 A | 7/1998 | Frid-Nielson et al. | |
| 5,781,442 A | 7/1998 | Engleson et al. | |
| 5,781,890 A | 7/1998 | Nematbakhsh et al. | |
| 5,802,253 A | 9/1998 | Gross et al. | |
| 5,823,948 A | 10/1998 | Ross, Jr. et al. | |
| 5,832,450 A | 11/1998 | Myers et al. | |
| 5,833,599 A | 11/1998 | Schrier et al. | |
| 5,835,898 A * | 11/1998 | Borg et al. | 705/7.12 |
| 5,838,313 A | 11/1998 | Hou et al. | |
| 5,842,173 A * | 11/1998 | Strum et al. | 705/2 |
| 5,845,253 A | 12/1998 | Rensimer et al. | |
| 5,848,393 A | 12/1998 | Goodridge et al. | |
| 5,848,395 A | 12/1998 | Edgar et al. | |
| 5,850,221 A | 12/1998 | Macrae et al. | |
| 5,867,688 A | 2/1999 | Simmon et al. | |
| 5,867,821 A | 2/1999 | Ballantyne et al. | |
| 5,899,998 A | 5/1999 | McGauley et al. | |
| 5,915,240 A | 6/1999 | Karpf | |
| 5,924,074 A | 7/1999 | Evans | |
| 5,946,659 A | 8/1999 | Lancelot et al. | |
| 5,970,466 A * | 10/1999 | Detjen et al. | 705/7.19 |
| 5,983,210 A | 11/1999 | Imasaki et al. | |
| 5,997,446 A | 12/1999 | Stearns | |
| 5,997,476 A | 12/1999 | Brown | |
| 5,999,916 A | 12/1999 | Peters et al. | |
| 6,014,631 A | 1/2000 | Teagarden et al. | |
| 6,016,477 A | 1/2000 | Ehnebuske et al. | |
| 6,021,404 A | 2/2000 | Moukheibir | |
| 6,035,278 A * | 3/2000 | Mansour | 705/9 |
| 6,037,940 A | 3/2000 | Schroeder et al. | |
| 6,047,259 A | 4/2000 | Campbell et al. | |
| 6,063,026 A | 5/2000 | Schauss et al. | |
| 6,067,523 A | 5/2000 | Bair et al. | |
| 6,076,105 A * | 6/2000 | Wolff et al. | 709/223 |
| 6,082,776 A | 7/2000 | Feinberg | |
| 6,139,494 A | 10/2000 | Cairnes | |
| 6,154,726 A | 11/2000 | Rensimer et al. | |
| 6,182,047 B1 | 1/2001 | Dirbas | |
| 6,188,988 B1 | 2/2001 | Barry et al. | |
| 6,263,330 B1 | 7/2001 | Bessette | |
| 6,283,761 B1 | 9/2001 | Joao | |
| 6,289,368 B1 | 9/2001 | Dentler et al. | |
| 6,304,905 B1 | 10/2001 | Clark | |
| 6,317,719 B1 | 11/2001 | Schrier et al. | |
| 6,332,167 B1 | 12/2001 | Peters et al. | |
| 6,345,260 B1 | 2/2002 | Cummings, Jr. et al. | |
| 6,401,072 B1 | 6/2002 | Haudenschild et al. | |
| 6,415,275 B1 | 7/2002 | Zahn | |
| 7,174,303 B2 * | 2/2007 | Glazer et al. | 705/9 |
| 7,225,220 B2 * | 5/2007 | Gonzalez et al. | 709/202 |
| 7,313,530 B2 * | 12/2007 | Smith et al. | 705/7 |
| 7,353,183 B1 * | 4/2008 | Musso | 705/9 |
| 7,359,864 B2 * | 4/2008 | Carlson et al. | 705/9 |
| 7,457,765 B2 * | 11/2008 | Thompson et al. | 705/7.14 |
| 7,676,391 B1 * | 3/2010 | Grunspan et al. | 705/8 |
| 2001/0016056 A1 | 8/2001 | Westphal et al. | |
| 2001/0016853 A1 | 8/2001 | Kucala | |
| 2001/0049610 A1 | 12/2001 | Hazumi | |
| 2001/0049619 A1 * | 12/2001 | Powell et al. | 705/9 |
| 2001/0051888 A1 | 12/2001 | Mayhak, Jr. et al. | |
| 2001/0056433 A1 | 12/2001 | Adelson et al. | |
| 2002/0001375 A1 | 1/2002 | Alcott et al. | |
| 2002/0001387 A1 | 1/2002 | Dillon | |
| 2002/0002473 A1 | 1/2002 | Schrier et al. | |
| 2002/0002478 A1 * | 1/2002 | Swart et al. | 705/8 |
| 2002/0002535 A1 | 1/2002 | Kitchen et al. | |
| 2002/0007287 A1 | 1/2002 | Straube et al. | |
| 2002/0152305 A1 * | 10/2002 | Jackson et al. | 709/224 |
| 2002/0165757 A1 * | 11/2002 | Lisser | 705/10 |
| 2003/0006988 A1 * | 1/2003 | Alford et al. | 345/440 |
| 2003/0069773 A1 * | 4/2003 | Hladik et al. | 705/7 |
| 2003/0088440 A1 | 5/2003 | Dunn | |
| 2003/0135382 A1 * | 7/2003 | Marejka et al. | 705/1 |
| 2004/0039628 A1 * | 2/2004 | Thompson et al. | 705/9 |
| 2004/0061891 A1 * | 4/2004 | Philpot | 358/1.15 |
| 2004/0102983 A1 * | 5/2004 | Carlson et al. | 705/1 |
| 2004/0117046 A1 * | 6/2004 | Colle et al. | 700/99 |
| 2004/0199416 A1 * | 10/2004 | Heina et al. | 705/10 |
| 2005/0015504 A1 * | 1/2005 | Dorne et al. | 709/229 |
| 2005/0065832 A1 * | 3/2005 | Virta | 705/8 |
| 2006/0041668 A1 * | 2/2006 | Dinger et al. | 709/229 |
| 2007/0208604 A1 * | 9/2007 | Purohit et al. | 705/9 |

FOREIGN PATENT DOCUMENTS

| | | |
|---|---|---|
| WO | WO 99/22330 | 5/1999 |
| WO | WO 99/44162 | 9/1999 |
| WO | WO 99/63473 | 12/1999 |
| WO | WO 00/28460 | 5/2000 |
| WO | WO 00/29983 | 5/2000 |
| WO | WO 00/65522 | 11/2000 |

OTHER PUBLICATIONS

Tyler et al., Determining Optimum Operating Room Utilization (2003), International Anesthesia Research Society, vol. 96, pp. 1114-1121.*
Acute Software, "Sun Solutions Catalog", 12 pages.
Andrew, et al., "Computer-based Patient Records—Venturing Off the Beaten Path: It's Time to Blaze New CPR Trails", Healthcare Informatics, 17 pages, May 1997.
"Autonomy Update", Product Brief, 3 pages.
"Brio.Portal", Product Information sheet, 1 page.
"CDR-Web", Reliance Software Systems, 1 page, 2000.
"Census Management", DINMAR (U.S.) Inc., 2 pages, 2002.
Cerner, "Acute Care EMR Solutions", 2 pages.
"Clinician Documentation with EMR", CliniComp, Int., 1 page, 1999-2002.
"Clinician Documentation with EMR", ClinicComp, Intl., 1 page, 1999-2002.
CMRxp—Computerized Medical Records Powered by Experience!!, Electronic Medical Records (EMR)xp Experience, ChartCare Inc., 2 pages, Mar. 5, 2003.
"DR-InBasket-Lab Results, Messaging and To-Do's", ChartCare Inc., 3 pages, Mar. 5, 2003.
Eclipsys, Advanced Clinical Solutions, "Sunrise Knowledge-based Orders", 4 pages.
Eclipsys, Advanced Clinical Solutions, "Sunrise Clinical Manager", 4 pages.
Eclipsys, News & Events, Press Releases, 3 pages, Apr. 16, 2002.
"EMR Features", Care is #1, 1 page, 1999, 2000.
"Enterprise Systems Management", Cerner Technologies, 5 pages, 2001.
"Essentris(TM) CPOE", CliniComp, Intl., 2 pages, 1999-2002.
"Essentris(TM) GDR", CliniComp, Int., 2 pages, 1999-2002.
ExcelCare Windows, 2 pages.

(56) References Cited

OTHER PUBLICATIONS

Expeditor Systems—The Patient Flow Systems Experts, 3 pages, 2001.
Grimson, et al., "Interoperability Issues in Sharing Electronic Healthcare Records—the Synapses Approach", IEEE, pp. 180-185, 1997.
Hazumi, et al., "Development of Electronic Medical Record System", NEC Res. & Develop. 41(1):102-105, 2000.
HealthMatics(TM) Office, 3 pages.
IC-Chart Additional Modules, InteGreat Inc., 1 page, 2003.
IDX, "Foundation", 2 pages.
IDX, "Supporting the Work of Clinicians", 1 page.
InteGreat—IC-Chart(TM) Information, 1 page.
"Intensivist Tools", CliniComp, Intl., 2 pages, 1999-2002.
Johnson, "Today's CDRS: The Elusive 'Complete' Solutions", Healtcare Informatics, 7 pages, Jul. 1997.
"LabTrack—Lab Ordering & Results Tracking", LabTrack—Lab Result Tracking Software, ChartCare Inc., 3 pages, Mar. 5, 2003.
"Location of JMJ Technologies—EncounterPRO, the Workflow Enabled CPR/EMR from JMJ Technologies", 6 pages, www.jujtech.com.
"Managing Mail Messages with Rules", Microsoft Outlook Help Manual, 5 pages, Version 6.
Marietti, "'O' Pioneers!", Healthcare Informatics, 9 pages, May 1999.
McDonald, et al., "The Regenstrief Medical Record System: A Quarter Century Experience", Inter. J. Med. Informatics 54:225-253, 1999.
McKesson, "Horizon Clinicals", 2 pages, Apr. 21, 2003.
Mercando, "Appointment Scheduling on Computer", PACE 20:1860-1862, 1997.
"PatInfo—Patient Information Handouts", PatInfo—Patient Demographics Software, ChartCare Inc., 2 pages, Mar. 5, 2003.
"Patient Lists", Epic Systems Corp., EpicCare Inpatient Electronic Medical Record Jul. 2000 User's Guide, Section 11.3-11.4, 3 pages.
"Portal-in-a-Box", Product Brief, 6 pages.
"Recall—Patient Health Maintenance", ChartCare Inc., 3 pages, Mar. 5, 2003.
"Rx—MedTrack—Prescription Writing/Medication Tracking", Rx—MedTrack—Prescription Writing Software, ChartCare Inc., 2 pages, Mar. 5, 2003.
"Services", InteGrate Inc., 2 pages, 2003.
"The Right Tools", Product Description, InteGreat Inc., 1 page, 2003.
"Working with Patient Lists", Epic Systems Corp., EpicCare Inpatient Electronic Medical Record Jul. 2000 Uer's Guide, Section 10.5-10.6, 3 pages.
Kaiser Permanente, Request of Cancer Appointments Online, 2 pages.

\* cited by examiner

220
Scheduling Screen: Dr. Peters

221 — Enter scheduling information:

222 — Patient ID: 09-994847

224 — Appointment Type: Colonoscopy

226 — Date: 7-03-04

228 — Time: 8-9AM

230 — Physician: Peters

233 — . . .

76%

Clear  Cancel  Enter
232  234  236

Utilization Percentage Database
7/01/04-7/07/04

| Doctor | Monday 7-1 | Tuesday 7-2 | Wednes. 7-3 | Thursday 7-4 | Friday 7-5 |
|---|---|---|---|---|---|
| Johnston | 76 | 92 | 84 | 84 | 16 |
| Peters | 76 | 50 | 76 | 84 | 42 |
| Arhamson | 24 | 16 | 48 | 32 | 48 |
| Philley | 84 | 84 | 16 | 64 | 64 |
| Tabor | 16 | 92 | 48 | 92 | 92 |

UTILIZATION INDICATING SCHEDULE SCANNER

CROSS-REFERENCE TO RELATED APPLICATIONS

This patent is related to provisional patent application 60/604,154 that is titled "Utilization Indicating Schedule Scanner" and that was filed on Aug. 24, 2004.

STATEMENT REGARDING FEDERALLY SPONSORED RESEARCH OR DEVELOPMENT

Not applicable.

BACKGROUND OF THE INVENTION

The field of the invention is scheduling systems and methods and more specifically scheduling systems that provide queues regarding how to optimally schedule appointments given current schedule status.

Historically, medical facilities scheduled appointments with clients by filling the next available schedule time slot if the slot fit into the client's schedule. Thus, if a client called to schedule a routine appointment for a physical and the next available slot occurred on a Friday two weeks after the date on which the client called to schedule the appointment, irrespective of how full the Friday schedule was, the appointment would be scheduled.

While scheduling appointments during next available time slots seems to make sense from the perspective of compressing physician schedules and increasing facility profitability, such scheduling practices also have some adverse consequences. First, in many cases unscheduled appointments have to be accommodated on an emergency or other basis. For instance, assume that a family health physician provides services to a family with an infant and that the infant wakes up one morning with a rash. In this case, the physician may simply instruct the parents over the phone to take some corrective action. If the rash persists, the parents may want to visit the physician during the physician's normally scheduled day and as quickly as possible.

Here, if the physician's schedule is completely booked for the next three weeks, one way to schedule an appointment for the infant in the near future is to squeeze the appointment in between already scheduled appointments on one of the fully scheduled days. Squeezing appointments in between existing appointments during a fully scheduled day is not a great option as the appointment with the infant and the other appointments end up being shorter than the time typically allotted or the appointments that occur after the infant's appointment end up being pushed back on the schedule. Where appointments are shortened or pushed back, clients are inconvenienced, understandably disappointed and, in some cases, receive or at least perceive reception of poorer services.

Another way to schedule an appointment for the infant is to extend the physician's day to add an appointment time slot either at the beginning or at the end of the day. Unfortunately many physicians already have demanding schedules and do not usually like to extend their office hours. In addition, medical offices often have regular hours during which staff is present and extending appointments beyond the usual office hours is administratively difficult.

Second, even where medical needs are not urgent, at least some clients like to schedule medical appointments as soon as they can after recognizing the need for consultation. Thus, for instance, where a client decides to have a routine physical performed, the client may want to have the physical performed in the next two days. As another instance, if a client wakes up one morning with pain in his thigh, while the pain may not amount to an emergency condition, the client may be anxious to identify the cause of the pain. Here, also, if the patient were forced to schedule an appointment two weeks after the pain in initially experienced, the pain may no longer be present and the cause likely would not be determinable. In either of these two cases, the same two options, squeezing in an additional appointment or extending the working day, are available to accommodate the client and the same problems result.

To accommodate emergency type appointments as well as demanding clients, many facilities have adopted scheduling policies whereby at least some schedule times are purposefully left open in each working day at least until a time temporally proximate the working day. Here, when a client calls to schedule an appointment, if the appointment is not urgent and the client is willing to attend an appointment in a few weeks, the scheduler may schedule the appointment in a few weeks even if there are open schedule time slots during the next few days. To this end, in known systems, after the scheduler determines that the client is willing to attend an appointment in a few weeks, the scheduler visually examines schedule information to identify a day that has multiple unscheduled time slots, suggests one or more of the identified time slots to the client and then schedules an appointment when appropriate.

In the above example, if the client has an urgent condition or has a strong preference to schedule an appointment sooner than a few weeks from the date when the client calls to schedule the appointment, the scheduler may schedule the appointment on the day on which the client attempts to make the appointment or on some day shortly thereafter. Thus, both emergency appointments and demanding clients can be accommodated by simply maintaining some schedule time slots open until there is some appropriate reason to fill them.

While scheduling procedures that purposefully maintain open slots have advantages, such procedures have several shortcomings. First, if schedule time slots that are purposefully maintained open are not filled, physician time is not most efficiently used. Thus, for instance, assume that a middle appointment time and a last appointment time during each of a physician's morning and afternoon schedules are maintained open unless necessarily filled to accommodate an emergency or a demanding client. Here, if the middle and last appointment times are not filled, the physician's time is wasted as the physician waits for the next scheduled appointment.

Second, while the scheduler may know the scheduling rules well, applying those rules efficiently can pose a challenge. For instance, where facility scheduling rules call for maintaining four appointment times open during each physician's day, in known systems, the scheduler has to manually examine daily schedules to determine if more than four schedule time slots are open on each day that the scheduler considers for scheduling an appointment. This process is tedious, can be time consuming and mistakes can be made.

Third, while it may be possible for schedulers to abide by simple scheduling procedures (e.g., maintaining at least four open time slots each day), conforming to more complex procedures would be difficult if not impossible in many cases. For instance, scheduling optimization may ideally require application of ten different yet related scheduling rules which would be extremely difficult for a scheduler to manually apply.

Thus, it would be advantageous to have a system that automatically applies scheduling preference or optimization rules to schedules to identify optimal scheduling time slots for appointments and that provides visual queues to a scheduler regarding scheduling preferences and optimal time slots thereby facilitating optimized scheduling procedures.

BRIEF SUMMARY OF THE INVENTION

It has been recognized that various aspects of physician's schedules can be used to identify optimization indicators for schedule sub-periods that can then be provided to schedulers to suggest optimal scheduling practices. For instance, in at least some cases the optimization indicators may indicate a utilization percentage that, as the label implies, is a percentage of currently scheduled time during a schedule sub-period where a sub-period may be any duration that occurs during a schedule that is of interest. For instance, in some cases, a sub-period may be a day while in other cases the sub-period may be a week. In still other cases the sub-period may be a portion of a day (e.g., morning, afternoon, etc.). Where the utilization percentage is high, a scheduler can be trained to recognize that scheduling during an associated sub-period is not encouraged and where the utilization percentage is low the scheduler can be trained to recognize that scheduling is encouraged. Other types of optimization indicators are contemplated including color coded indicators that provide quick visual cues regarding scheduling optimization. In addition, optimization indicators based on other than utilization percentage or on a plurality of factors are contemplated.

Consistent with the above, at least some embodiments of the invention include a method for use with a processor, a database and an interface including a display screen, the database including schedule information associated with utilization of time for at least one medical resource that may be scheduled for use over a period including several sub-periods, the method for aiding a scheduler responsible for scheduling the resource to optimally schedule new requests for the resource's time, the method comprising the steps of identifying a utilization value for at least one schedule sub-period for the at least one resource wherein the utilization value indicates current use of time for the at least one sub-period for the at least one resource, identifying an optimization indicator at least in part as a function of the utilization value for the at least one sub-period and presenting the optimization indicator via the display.

In some cases the utilization value is a utilization percentage of the at least one sub-period. In some cases the scheduler is affiliated with the entity that controls the resource, the method further including receiving a scheduling request from a client attempting to identify availability of the resource for an appointment to be scheduled. In some cases the scheduler is a client attempting to identify availability of the resource for an appointment that the client desires to schedule and wherein the step of presenting the optimization indicator includes providing a network link between the processor and the interface and presenting the optimization indicator remotely to the client.

In some cases the resource is a medical service provider and wherein the step of identifying a utilization value includes identifying the percent utilization of the providers time over the at least one sub-period. Here, the step of presenting an optimization indicator may include presenting a visually distinct indicator where the distinction is a function of the value of the utilization percentage. Here, the step of presenting an optimization indicator may include presenting a color coded icon wherein the color of the icon depends at least in part on the utilization percentage. Moreover, there may be a plurality of different percentage ranges and wherein the color of each icon depends at least in part on the range that includes an associated utilization percentage. In addition, the ranges and the colors may be selectable by the scheduler. Furthermore, the step of presenting an optimization indicator may also include indicating the utilization percentage via a percentage number. In some cases the percentage number is placed within the color coded icon.

In some cases the step of identifying an optimization indicator includes identifying the optimization indicator at least in part as a function of the period between a reference time and the time of the at least one sub-period. In some cases the reference time is the current time. In some cases the step of identifying the percentage of time utilization for at least one of the sub-periods and the at least one provider includes identify the percentage of time utilization for a subset of sub-periods for the at least one provider, the step of identifying includes identifying a separate optimization indicator for each of a plurality of sub-periods, the step of presenting including simultaneously presenting an optimization indicator for at least a subset of the plurality of the sub-periods. Here, the step of identifying the percentage of time utilization for a plurality of sub-periods for the at least one provider may include identifying the percentage of time utilization for a plurality of sub-periods for each of a plurality of providers, the step of identifying includes identifying a separate optimization indicator for each of a plurality of sub-periods for each of the plurality of providers, the step of presenting including simultaneously presenting an optimization indicator for at least a subset of the plurality of the sub-periods for at least a subset of the providers. In some cases the providers, sub-periods and optimization indicators are presented in a table format. In some cases the table format includes a column of time providers, a row of sub-periods and a separate optimization indicator for each of the sub-periods and each of the providers. In some cases the interface includes an input device for selecting information on the display, the method further including monitoring the interface for selection of one of the providers and, when a provider is selected, moving the selected provider and associated optimization indicators to the top of the table. In some cases the interface includes an input device for selecting information on the display, the method further including monitoring the interface for selection of one of the sub-periods and, when a sub-period is selected, ordering the providers in the table as a function of the optimization indicators that occur during the selected sub-period.

In some cases the method is for use as an enhancement to a scheduling program, the interface including an input device for selecting information on the display, the method further including the steps of monitoring the interface for selection of one of the optimization indicators and, when an optimization indicator is selected, presenting schedule information for the provider and the sub-period associated with the selected optimization indicator.

In some embodiments the step of identifying each of the optimization indicators includes identifying a color wherein different colors indicate different levels of optimization. Here, there may be a plurality of different utilization percentage ranges and wherein the color of each associated optimization indicator depends at least in part on the range that includes an associated utilization percentage. In some cases the optimization indicators are presented in separate table cells and wherein each cell is colored with the associated optimization indicator color. In some cases the sub-periods are days of the week. In some cases the colors associated with each of the optimization indicators are at least in part a function of the period between a reference time and the time of the sub-process. In some embodiments the reference time is the current time.

In some embodiments the invention includes an enhancement to a scheduling program, the method further including the step of, when the portion of the schedule associated with the at least one sub-period is modified, altering the utilization value associated with the sub-period to reflect the modification and storing a new utilization value for the at least one resource and the at least one sub-period. Here, the step of identifying a utilization value may include identifying a utilization percentage that is the percent of the sub-period currently scheduled wherein the resource's time is scheduled in block-periods where each block-period includes a block percentage of the duration of the sub-period, the step of altering the utilization percentage including, when a block-period is scheduled, adding the block-percentage to the utilization percentage to identify a new utilization percentage.

In some cases the invention is for use as an enhancement to scheduling software wherein the step of identifying a utilization value includes identifying a utilization percentage for each of a plurality of sub-periods, the step of identifying an optimization indicator including identifying an optimization indicator for each of the utilization percentages and the step of presenting the optimization indicator including presenting an optimization indicator each time information for a corresponding sub-period is displayed. In some instances the method is for use as an enhancement to scheduling software wherein the step of presenting the optimization indicator includes presenting the optimization indicator each time information corresponding to the at least one of the sub-periods is displayed.

In some cases the method is for use as an enhancement to scheduling software, the method further including the step of receiving via the interface at least one characteristic of an appointment to be scheduled wherein the step of identifying an optimization indicator includes identifying an optimization indicator at least in part as a function of the appointment characteristic. In some cases the step of receiving at least one characteristic of an appointment includes determining the duration an appointment to be scheduled, the step of identifying an optimization indicator including identifying a possible utilization value that reflects the current utilization value and the duration of the appointment. In some cases the step of identifying a possible utilization value includes identifying a possible utilization percentage that reflects the current utilization value and the duration of the appointment.

In some cases the method further includes the step of, prior to identifying, receiving a selection from the scheduler selecting the at least one resource from a list of resources and the at least one of the sub-periods.

Some embodiments include a method for use with a processor, a database and an interface including a display screen, the database including schedule information associated with utilization of time for a plurality of medical resources that may be scheduled for use over a period including several sub-periods, the method for aiding a scheduler responsible for scheduling use of the resource to optimally schedule new requests for the resource's time, the method comprising the steps of providing an input device by which the scheduler can select a sub-set of the sub-periods, receiving a selection of a subset of the sub-periods, identifying a utilization value for each of the subset sub-periods for at least a sub-set of the resources, identifying an optimization indicator for each of the utilization values at least in part as a function of the utilization values of the sub-periods and presenting at least a subset of the optimization indicators via the display.

In some cases utilization value is a utilization percentage indicating the utilization of an associated sub-period that is currently scheduled. In some embodiments the method is for use as an enhancement to scheduling software, the method further including the step of receiving via the interface at least one characteristic of an appointment to be scheduled wherein the step of identifying an optimization indicator includes identifying an optimization indicator at least in part as a function of the appointment characteristic.

In some cases the step of receiving at least one characteristic of an appointment includes determining the duration of an appointment to be scheduled, the step of identifying an optimization indicator including identifying a possible utilization percentage that reflects the current utilization percentage and the duration of the appointment.

In some cases the resources are medical service providers and wherein the step of identifying a utilization percentage for each of the subset sub-periods for at least a sub-set of the resources includes identifying a utilization percentage for each of the subset sub-periods for at least a sub-set of the medical service providers. In some cases the step of presenting optimization indicators includes presenting a table including a separate optimization indicator for each combination of a resource and a sub-period presented via the display. In some cases the step of identifying optimization indicators includes identifying a color at least in part as a function of an associated utilization percentage and wherein the step of presenting optimization indicators includes presenting icons having the identified colors. In some cases the colors associated with the optimization indicators are also at least in part dependent upon the duration of a period between a reference time and the associated sub-periods. In some embodiments the input device is also useable to select the sub-set of providers, the method further including the step of receiving a selection of the provider sub-set.

Some embodiments of the invention include a method for use with a processor, a database and an interface including a display screen, the database including schedule information associated with utilization of time for at least one medical resource that may be scheduled for use over a period including several sub-periods, the method for aiding a scheduler responsible for scheduling use of the resource to optimally schedule new requests for the resource's time, the method comprising the steps of identifying the duration of an intervening period between a reference time and at least one of the sub-periods, identifying an optimization indicator at least in part as a function of the intervening period and presenting the optimization indicator via the display.

Some embodiments include a method for use with a processor, a database and an interface including a display screen, the database including schedule information associated with utilization of time for at least one medical resource that may be scheduled for use over a period including several sub-periods, the method for aiding a scheduler responsible for scheduling use of the resource to optimally schedule new requests for the resource's time, the method comprising the steps of identifying a utilization value for at least one schedule sub-period for the at least one provider wherein the utilization value is at least a function of a current percentage of time utilization for the at least one sub-period for the at least one resource, identifying an optimization indicator at least in part as a function of the utilization value for the at least one sub-period, presenting the optimization indication via the display, receiving a command to modify the resource's schedule during the at least one sub-period, altering the current utilization value as a function of the received command and storing the altered utilization value as a new current utilization value for the sub-period for subsequent use.

In some cases each utilization value is a utilization percentage indicating the utilization of an associated sub-period that is currently scheduled. In some cases the step of identifying an optimization indicator includes receiving an indication of the duration of an appointment to be scheduled and identifying an optimization indicator at least in part as a function of the duration. In some cases the at least one resource's time is scheduled in block-periods where each block-period includes a block percentage of the duration of the sub-period, the step of altering the utilization percentage including, when a block-period is scheduled, adding the block-percentage to the utilization percentage to identify a new utilization percentage. In some cases the steps of altering and storing are performed prior to receiving a following command to modify the resource's schedule.

Some embodiments also include a method for use with a processor, a database and an interface including a display screen, the database including schedule information associated with utilization of time for a plurality of medical resources that may be scheduled for use over a period including several sub-periods, the method for aiding a scheduler responsible for scheduling use of the resources to optimally schedule new requests for the resources' time, the method comprising the steps of identifying a utilization value for at least one schedule sub-period for each of the resources wherein the utilization value reflects the currently scheduled utilization of an associated sub-period, identifying optimization indicators for each of the utilization percentages at least in part as a function of the utilization percentages and presenting at least a subset of the optimization indicators via the display.

In some cases each utilization value is a utilization percentage indicate current percentages of time utilization for the sub-periods for the resources. In some cases the step of presenting includes presenting a table include a column listing the providers, a heading row listing the sub-periods and a separate optimization cell associated with each of the providers and each of the sub-periods and presenting an optimization indicator in each of the optimization cells corresponding to each provider-sub-period combination. In some cases the step of presenting an indication further includes at least in part coloring each of the optimization cells where the colors of the cells are at least in part a function of the associated utilization percentages. In some cases there are a plurality of different percentage ranges and wherein the color associated with each cell depends on the range that includes an associated utilization percentage. In some cases each cell is filled in with the associated color. In some cases the step of presenting optimization indicators also includes indicating the utilization percentages via corresponding numbers placed within the cells.

Some embodiments include a method for use with a processor, a database and an interface including a display screen, the database including schedule information associated with utilization of time for at least one medical resource that may be scheduled for use over a period including several sub-periods, the method for aiding a scheduler responsible for scheduling use of the resource to optimally schedule new requests for the resource's time, the method comprising the steps of providing a rule set for determining how optimal sub-periods are for scheduling appointments, for each of a plurality of sub-periods, identifying an optimization indicator as a function of the rule set and presenting at least a subset of optimization indicators via the display.

Some embodiments include the step of providing a rule set includes providing a rule set that takes into consideration at least a subset of the current sub-period utilization percentage of a sub-period, the current sub-period utilization percentages of sub-periods temporally proximate other sub-periods, intervening periods between a current time and when sub-periods occur, distribution of current appointments during a sub-period, multiple physician schedules, duration of an appointment to be scheduled, requirements for scheduling other temporally proximate appointments for a first specific client and requirements for scheduling other temporally proximate appointments for a second specific client where the second client is different than the first client.

In some cases the optimization indicators include colored elements where different colors indicate different degrees of optimizations.

Some embodiments include a method for use with a processor, a database and an interface including a display screen, the database including schedule information associated with utilization of time for at least one medical resource that may be scheduled for use over a period including several sub-periods, the method for aiding a scheduler responsible for scheduling use of the resource to optimally schedule new requests for the resource's time, the method comprising the steps of determining how optimal sub-periods are for scheduling appointments and indicating via the display relative degrees of optimization for at least a subset of the sub-periods.

Other embodiments include a method for use with a processor, a database and an interface including a display screen, the database including schedule information associated with utilization of time for at least one medical resource that may be scheduled for use over a period including several sub-periods, the method for aiding a scheduler responsible for scheduling the resource to optimally schedule new requests for the resource's time, the method comprising the steps of identifying a current utilization value for at least one schedule sub-period for the at least one resource wherein the utilization value indicates current use of time for the at least one sub-period for the at least one resource, receiving an indication of the duration of an appointment to be scheduled, identifying a possible utilization value as a function of the current utilization value and the duration of the appointment, identifying an optimization indicator at least in part as a function of the possible utilization value for the at least one sub-period and presenting the optimization indicator via the display. In some cases each utilization value is a utilization percentage indicating current percentages of time utilization for the sub-periods for the at least one resource.

Some embodiments include an apparatus for aiding a scheduler responsible for scheduling at least one resource to optimally schedule new requests for the resource's time, the apparatus comprising an interface, a display screen, a database including schedule information associated with utilization of time for at least one resource that may be scheduled for use over a period including several sub-periods and a processor programmed to perform the steps of identifying a utilization value for at least one schedule sub-period for the at least one resource wherein the utilization value indicates current use of time for the at least one sub-period for the at least one resource, identifying an optimization indicator at least in part as a function of the utilization value for the at least one sub-period and presenting the optimization indicator via the display.

In some cases the utilization value is a utilization percentage of the at least one sub-period. In some cases the scheduler is a client attempting to identify availability of the resource for an appointment that the client desires to schedule, the apparatus further including a network that links the interface and display to the processor, the processor programmed to perform the step of presenting the optimization indicator by linking to the interface via the network and presenting the optimization indicator remotely to the client. In some cases the resource is a medical service provider and wherein the processor identifies a utilization value by identifying the percent utilization of the providers time over the at least one sub-period. In some cases the processor presents an optimization indicator by presenting a visually distinct indicator where the distinction is a function of the value of the utilization percentage. In some cases the processor presents an optimization indicator by presenting a color coded icon wherein the color of the icon depends at least in part on the utilization percentage. In some cases there are a plurality of different percentage ranges and wherein the color of each icon depends at least in part on the range that includes an associated utilization percentage. In some cases the processor presents an optimization indicator by indicating the utilization percentage via a percentage number. In some cases the percentage number is placed within the color coded icon. In some cases the processor identifies an optimization indicator by identifying the optimization indicator at least in part as a function of the period between a reference time and the time of the at least one sub-period. In some cases the reference time is the current time.

In some cases the method is for use as an enhancement to a scheduling program, the processor further programmed to perform the steps of, when the portion of the schedule associated with the at least one sub-period is modified, altering the utilization value associated with the sub-period to reflect the modification and storing a new utilization value for the at least one resource and the at least one sub-period. In some cases the processor identifies a utilization value by identifying a utilization percentage that is the percent of the sub-period currently scheduled wherein the resource's time is scheduled in block-periods where each block-period includes a block percentage of the duration of the sub-period, the processor altering the utilization percentage by, when a block-period is scheduled, adding the block-percentage to the utilization percentage to identify a new utilization percentage.

In some cases the method performed is for use as an enhancement to scheduling software wherein the processor identifies a utilization value by identifying a utilization percentage for each of a plurality of sub-periods, the processor identifying an optimization indicator by identifying an optimization indicator for each of the utilization percentages and the processor presenting the optimization indicator by presenting an optimization indicator each time information for a corresponding sub-period is displayed.

In some cases the method performed is for use as an enhancement to scheduling software wherein the processor presents the optimization indicator by presenting the optimization indicator each time information corresponding to the at least one of the sub-periods is displayed.

In some cases the method performed is for use as an enhancement to scheduling software, the processor further programmed to perform the step of receiving via the interface at least one characteristic of an appointment to be scheduled wherein the processor identifies an optimization indicator by identifying an optimization indicator at least in part as a function of the appointment characteristic. In some cases the processor receives the at least one characteristic of an appointment by determining the duration an appointment to be scheduled, the processor identifying an optimization indicator by identifying a possible utilization value that reflects the current utilization value and the duration of the appointment.

Some embodiments include an apparatus for aiding a scheduler responsible for scheduling use of at least one resource to optimally schedule new requests for the resource's time, the apparatus comprising an interface, a display screen, a database including schedule information associated with utilization of time for at least one resource that may be scheduled for use over a period including several sub-periods and a processor programmed to perform the steps of receiving a selection of a subset of the sub-periods via the interface, identifying a utilization value for each of the subset sub-periods for at least a sub-set of the resources, identifying an optimization indicator for each of the utilization values at least in part as a function of the utilization values of the sub-periods and presenting at least a subset of the optimization indicators via the display.

Other embodiments include an apparatus for aiding a scheduler responsible for scheduling use of the resource to optimally schedule new requests for the resource's time, the method comprising the steps of an interface, a display screen, a database including schedule information associated with utilization of time for at least one resource that may be scheduled for use over a period including several sub-periods and a processor programmed to perform the steps of receiving a selection of a subset of the sub-periods via the interface, identifying the duration of an intervening period between a reference time and at least one of the sub-periods, identifying an optimization indicator at least in part as a function of the intervening period and presenting the optimization indicator via the display.

In some cases the processor identifies an optimization indicator by identifying a color where different colors correspond to different intervening periods and wherein the processor presents by presenting a colored element that is visually associated with the at east one of the sub-periods. In some cases the processor is further programmed to perform the step of identifying a utilization percentage for the at least one sub-period wherein the utilization percentage indicates a current percentage of time utilization for the at least one sub-period for the at least one resource, the processor identifying an optimization indicator by identifying the indicator at least in part as a function of the utilization percentage. In some cases the method performed is for use as an enhancement to scheduling software, the processor further programmed to perform the step of receiving via the interface an indication of the duration of an appointment to be scheduled wherein the processor identifies an optimization indicator by identifying an optimization indicator at least in part as a function of the duration of the appointment to be scheduled. In some cases the processor identifies an intervening period by identifying intervening periods for a plurality of sub-periods, the processor identifying an optimization indicator by identifying a separate optimization indicator for each of the intervening periods and the processor presenting by presenting at least a subset of the identified optimization indicators such that the presented indicators are visually associated with corresponding sub-periods.

Some embodiments include apparatus for scheduling use of at least one resource to optimally schedule new requests for the resource's time, the apparatus comprising an interface, a display screen, a database including schedule information associated with utilization of time for at least one resource that may be scheduled for use over a period including several sub-periods and a processor programmed to perform the steps of identifying a utilization value for at least one schedule sub-period for the at least one provider wherein the utilization value is at least a function of a current percentage of time utilization for the at least one sub-period for the at least one resource, identifying an optimization indicator at least in part as a function of the utilization value for the at least one sub-period, presenting the optimization indication via the display, receiving a command via the interface to modify the resource schedule during the at least one sub-period, altering the current utilization value as a function of the received command and storing the altered utilization value as a new current utilization value for the sub-period for subsequent use. Here, in some cases each utilization value is a utilization percentage indicating the utilization of an associated sub-period that is currently scheduled. In some cases the processor identifies an optimization indicator by receiving an indication of the duration of an appointment to be scheduled and identifying an optimization indicator at least in part as a function of the duration. In some cases the at least one resource's time is scheduled in block-periods where each block-period includes a block percentage of the duration of the sub-period, the processor altering the utilization percentage by, when a block-period is scheduled, adding the block-percentage to the utilization percentage to identify a new utilization percentage.

Some embodiments include an apparatus for scheduling use of resources to optimally schedule new requests for the resources' time, the apparatus comprising an interface, a display screen, a database including schedule information associated with utilization of time for a plurality of resources that may be scheduled for use over a period including several sub-periods and a processor programmed to perform the steps of identifying a utilization value for at least one schedule sub-period for each of the resources wherein the utilization value reflects the currently scheduled utilization of an associated sub-period, identifying optimization indicators for each of the utilization percentages at least in part as a function of the utilization percentages and presenting at least a subset of the optimization indicators via the display. In some cases each utilization value is a utilization percentage indicate current percentages of time utilization for the sub-periods for the resources.

Some embodiments include an apparatus for scheduling use of the resource to optimally schedule new requests for the resource's time, the apparatus comprising an interface, a display screen, a database including schedule information associated with utilization of time for at least one resource that may be scheduled for use over a period including several sub-periods, the database also including a rule set for determining how optimal sub-periods are for scheduling appointments and a processor programmed to perform the steps of for each of a plurality of sub-periods, identifying an optimization indicator as a function of the rule set and presenting at least a subset of optimization indicators via the display. In some cases the rule set includes a rule set that takes into consideration at least a subset of the current sub-period utilization percentage of a sub-period, the current sub-period utilization percentages of sub-periods temporally proximate other sub-periods, intervening periods between a current time and when sub-periods occur, distribution of current appointments during a sub-period, multiple physician schedules, duration of an appointment to be scheduled, requirements for scheduling other temporally proximate appointments for a first specific client and requirements for scheduling other temporally proximate appointments for a second specific client where the second client is different than the first client.

Some embodiments include an apparatus for aiding a scheduler responsible for scheduling use of the resource to optimally schedule new requests for the resource's time, the apparatus comprising a display screen, a database including schedule information associated with utilization of time for at least one resource that may be scheduled for use over a period including several sub-periods and a processor programmed to perform the steps of determining how optimal sub-periods are for scheduling appointments and indicating via the display relative degrees of optimization for at least a subset of the sub-periods.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

BRIEF DESCRIPTION OF THE SEVERAL VIEWS OF THE DRAWINGS

FIG. 3 is a simplified and exemplary scheduling window that may be provided via the interface of FIG. 1;

FIG. 4 is a schematic diagram illustrating an exemplary utilization percentage database consistent with at least some aspects of the present invention;

DETAILED DESCRIPTION OF THE INVENTION

While the present invention may be embodied in any of several different forms, the present invention is described herewith the understanding that the present disclosure is to be considered as setting forth an exemplary embodiment which is not intended to limit the invention to the specific embodiment(s) illustrated. To this end, while the inventions are described herein in the context of medical resources that need to be scheduled and more specifically, physician time, it should be appreciated that the invention is broadly related to any type of schedulable resource.

Hereinafter, aspects of the present invention will be described in the context of a simplified scheduling system that keeps track of physician schedules for physicians that work at an exemplary medical facility in order to simplify this explanation. Nevertheless, it should be appreciated that the inventive aspects are intended to be used with simple as well as more complex scheduling systems. For example, while the inventions are described herein in the context of the system including a single scheduling server, it is contemplated that more than one server may maintain physician schedules and may be linked via the internet or the like. Similarly, while the information system is described in the context of a single medical facility, it should be appreciated that the system may be employed where a plurality of related medical facilities cooperate to provide services and where scheduling functions are provided across related facilities. As another example, while the simplified system is described as including a single scheduling interface, it should be appreciated that many different interfaces may be employed for scheduling purposes. Moreover, while the system is described in the context of physician schedules, other systems may be employed to track and suggest optimal scheduling times for virtually any type of resource to be scheduled including medical or industrial equipment, plane or vehicle rentals, etc.

Figure 1:
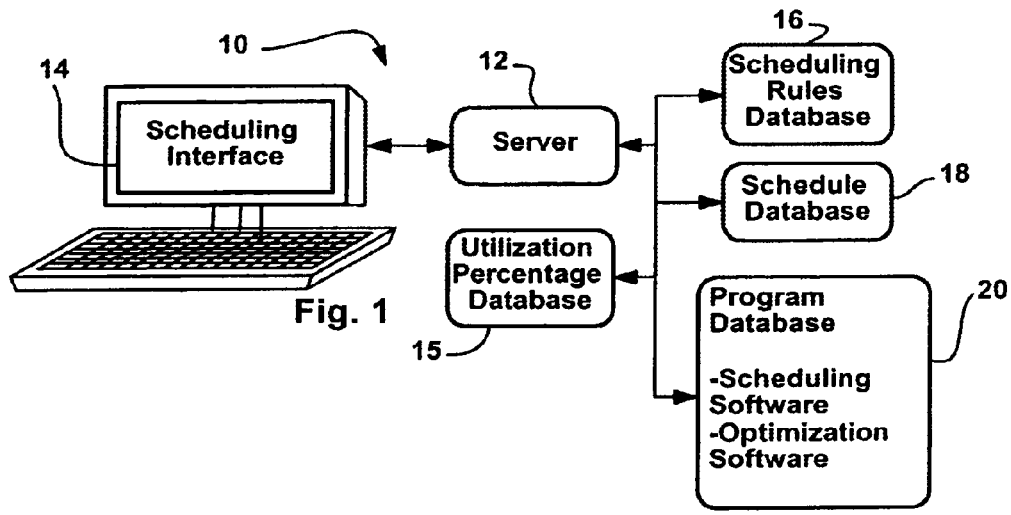
FIG. 1 is a schematic diagram illustrating a scheduling system used to implement various aspects of the present invention.

Referring now to the drawings wherein like reference numerals correspond to similar elements through the several views and, more specifically, referring to FIG. 1, the inventions will be described in the context of an exemplary scheduling system 10 including a server 12, a scheduling interface 14, a scheduling rules database 16, a schedule database 18 and a program database 20. Server 12 includes one or more high speed processors that run various programs to carry out methods that are consistent with the present invention. To this end, server 12 is linked via a computer network represented by lines in FIG. 1 to each of scheduling interface 14, scheduling rules database 16, schedule database 18 and program database 20. The programs run by server 12 are stored in program database 20 and include, among others, scheduling software and scheduling optimization software.

As the label implies, scheduling software is run by server 12 to maintain schedules for physicians that work at a medical facility associated with system 10. To this end, the scheduling software keeps track of schedules for each one of the facility physicians and allows a scheduler (i.e., a facility employee charged with maintaining the physician's schedules) to modify the schedule thereby adding appointments to the schedule and removing appointments from the schedule when appropriate.

Figure 2:
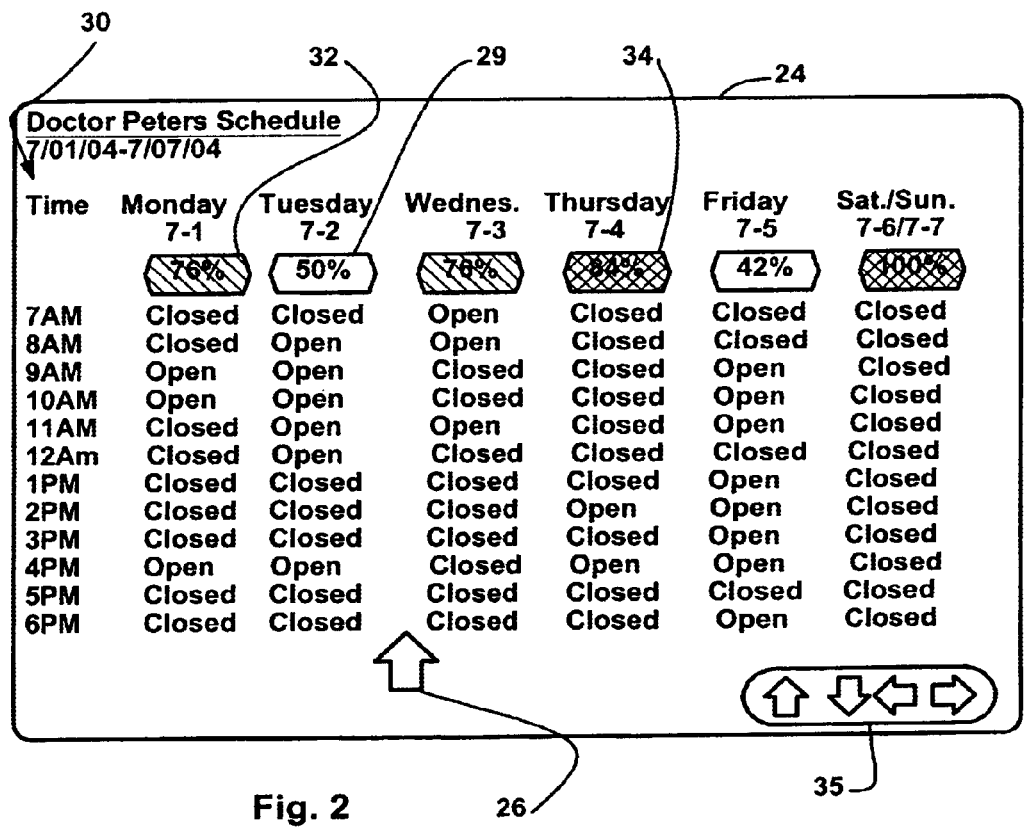
FIG. 2 is a doctor's schedule window that may be presented via the interface of FIG. 1 illustrating a schedule corresponding to a specific doctor that works at a medical facility associated with the system of FIG. 1.

Referring also to FIG. 2, an exemplary schedule window 24 that may be provided via interface 14 by server 12 running the scheduling software illustrates a seven day schedule for one of the facility physicians, Dr. Peters. Exemplary window 24 identifies Dr. Peters at the top of the window and includes a table including seven columns and a plurality of rows. The first column of the table is a time column which divides the time in a working day into one hour time slots including 7 AM, 8 AM, 9 AM, etc. Each of the second through sixth columns in the table is a working day of the week column while the seventh column is a weekend column corresponding to Saturday and Sunday. Thus, for instance, the second column in the table corresponds to Monday, the third column corresponds to Tuesday, etc.

The Monday column includes a status designation for each time slot in the time column where the status designations indicate either "OPEN" or "CLOSED". And OPEN status designation indicates that the time slot is open for Dr. Peters and that an appointment may be scheduled in that time slot. A CLOSED status designation indicates that Dr. Peters is not free to conduct an appointment during the associated time slot either because the doctor already has an appointment scheduled or because the doctor is not taking an appointment during that time. Similarly, status designations are provided in each of the other day columns (i.e., the third through seventh columns of the table) for each of the time slots in the first column of the table.

In addition to the doctor designation in the table described above, window 24 includes various interfacing or input tools that can be used by the scheduler to perform scheduling functions. To this end, an input device (e.g., a mouse, wireless tablet/hand held device, touch screen, track ball, etc.) controlled arrow or pointing cursor 26 (hereinafter "cursor") is illustrated which can be used (i.e., moved over an icon to select while a controlling mouse is double-clicked) to select one of the status designations in the table to either receive additional information about a closed time slot or to select one of the open time slots for scheduling an appointment. In addition, a multifunction scrolling icon 35 is provided that allows the scheduler to scroll through other days, weeks, months and hours of Dr. Peters' schedule. Other tools for scrolling through physician's schedules or for searching for specific information in physician schedules are contemplated and are not described here in the interest of simplifying this explanation.

Referring still to FIG. 2, to schedule an appointment with Dr. Peters on Wednesday, July 3, in the 8 AM time slot, a scheduler uses cursor 26 to select the "OPEN" status designation corresponding to the 8 AM time slot on Wednesday, July 3. When the "OPEN" designation is selected, referring to FIG. 3, a scheduling window 220 is opened. The exemplary scheduling window 220 indicates at the top that the window corresponds to Dr. Peters and includes a plurality of appointments specifying fields that can be filled in by the scheduler to schedule an appointment for Dr. Peters. In this regard, the exemplary scheduling widow 220 includes a patient ID field 222, an appointment type field 224, a date field 226, a time or time slot field 228 and a physician field 230. Here, information from the previous schedule windows (see again FIG. 2) can be used to automatically populate at least some of the scheduling fields. For example, because the scheduler selected the 8 AM time slot on Wednesday, July 3, the date and time fields 226 and 228, respectively, can automatically be filled in. In addition, physician field 230 can automatically be filled in as the scheduling screen window 224 corresponds to Dr. Peters. The scheduler fills in the remaining specifying fields with appointment specifying information. In the present example, the scheduler fills in the patient ID number 09-994847 in patient ID field 222 and a colonoscopy activity in appointment type field 224. In addition to the physician designation and specifying fields, cursor selectable CLEAR, CANCEL and ENTER icons 232, 234 and 236, respectively, are provided near the bottom of window 220. CLEAR icon 232 can be used to clear all of the information in the specifying fields above. CANCEL icon 234 can be used to cancel the current scheduling activity and return to the previous schedule window (e.g., see again FIG. 2). ENTER icon 236 is selectable to schedule an appointment consistent with the information specified in the fields of window 220.

Referring again to FIG. 1, the scheduling optimization software, as the label implies, analyzes the schedule stored in database 18 by comparing the scheduling rules from database 16 to the current schedule to identify optimal scheduling times for appointments to be scheduled and then provides suggestions to a scheduler via interface 14 regarding when appointments should be scheduled. For example, in at least some embodiments of the present invention, optimal scheduling is suggested by identifying the percentage of time slots during various schedule sub-periods and indicating, via "utilization percentage", the relative availability of time slots during each one of the sub-periods. For instance, in at least some embodiments, the schedule sub-periods will comprise working days (e.g., Monday, Tuesday, etc.) where time slots are one hour each and a working day begins at 7 AM and ends at 7 PM so that there are twelve separate one hour time slots during each working day. Here, where nine of the time slots on a specific day are closed and three are open, the utilization percentage is 76%, where 6 of the time slots on a day are closed and the other 6 are open, the utilization percentage is 50%, and so on.

Referring now to FIG. 4, in cases where utilization percentages are determined, server 12 stores current utilization percentages in utilization percentages database 15. Exemplary database 15 include a table having a plurality of columns and rows, the columns including a doctor or physician column 42 and a separate sub-period column corresponding to each of the working days in the schedules of the physicians. In FIG. 4, five days of the physician's schedules are illustrated including Monday through Friday, July 1 through July 5. In a complete database, a separate column would be provided for each working day of the year. The doctor column 42 lists all of the facility doctors including Dr. Peters. Each of the sub-period columns includes a separate utilization percentage for each one of the doctors in column 42. For example, for Dr. Peters in column 42, the Monday sub-period column indicates a 76% utilization percentage and the Thursday column indicates an 84% utilization percentage while, for Dr. Tabor, the Monday column indicates a 12% utilization percentage and the Thursday column indicates a 94% utilization percentage.

Referring to FIGS. 1 through 4, when Dr. Peters schedule is accessed via interface 14 and, more specifically, the portion of Dr. Peters schedule corresponding to Monday, July 1 through Sunday, July 7, in addition providing the schedule information for Dr. Peters as described above and as illustrated in FIG. 2, server 12 also provides an optimization indicator for each of the schedule days. To this end, server 12 accesses the utilization percentage database 15 and obtains the utilization percentages for Dr. Peters during the time period being analyzed by the scheduler. Consistent with the information in FIG. 4 for Dr. Peters, optimization indicators are provided just under the day and date designations in the window 24 of FIG. 2 where, the optimization indicators indicate that on Monday, Tuesday, Wednesday, Thursday and Friday, Dr. Peters current schedule has utilization percentages of 76%, 50%, 50%, 76%, 84% and 42%, respectively. On Saturday and Sunday, July 6 and 7, Dr. Peters does not work and therefore his entire schedule on those two days is closed and the utilization percentage indicated by the optimization indicator is 100%.

Thus, in at least some cases, very simple optimization indicators such as utilization percentages can be provided for specific sub-periods of a schedule for a specific doctor that can be used by a scheduler to quickly identify optimal sub-periods during which appointments should be scheduled. In this regard, assume that a medical facility has adopted very general scheduling rules whereby, unless absolutely necessary, because of an emergency situation or a particularly demanding client, the facility wants to maintain a few time slots open during each physician's working day until the specific working day occurs. In this case, referring again to FIG. 2, when the scheduler analyzes window 24 and, more specifically, the optimization indicators (i.e., the percentages), the scheduler can quickly identify that each of Tuesday and Friday have a relatively large number of open time slots compared to Monday, Wednesday and Thursday, and therefore, that it may be optimal to schedule an appointment during either Tuesday or Friday.

If the scheduler schedules an appointment for one of the open times on Friday, after the appointment is scheduled, server 12 updates the utilization percentage database to reflect the new state of Dr. Peters' schedule. In this regard, where a working day includes twelve one hour time slots, each one of the time slots corresponds to approximately 8% of the working day's schedule. Here, where one time slot during a day long sub-period is closed, the utilization percentage for that day can be modified by simply adding 8% to the initial utilization percentage. For instance, in the case of the Friday time slot in FIG. 2 where the initial utilization percentage is 42%, when one of the open time slots (e.g., 9 AM) is closed, the 42% utilization percentage can be incremented by 8% for a total 50% utilization percentage and the 50% percentage can be stored in database 15 for subsequent use.

In addition to providing schedule windows with optimization indicators as illustrated in FIG. 2, other views of physician schedules are contemplated wherein optimization indicators are provided to suggest optimal scheduling choices. In this regard, it is contemplated that scheduling software will typically provide several different data representations depending upon scheduler activities. Hereinafter, unless indicated otherwise, scheduler activity that results in presentation of schedule information will be referred to as a query. Thus, for instance, one query consistent with the window view of FIG. 2 would be to view Dr. Peters' schedule for July first through fifth of 2004. Other similar queries may be to observe Dr. Peters' schedule for a different five day period; for a two day period, for a specific day, for a month, etc. As still one other example, a query may be to observe scheduling information for a subset of facility physicians for a five day period. In each of these cases, in addition to providing schedule information, optimization indicators may be provided as part of each window view.

Figure 5:
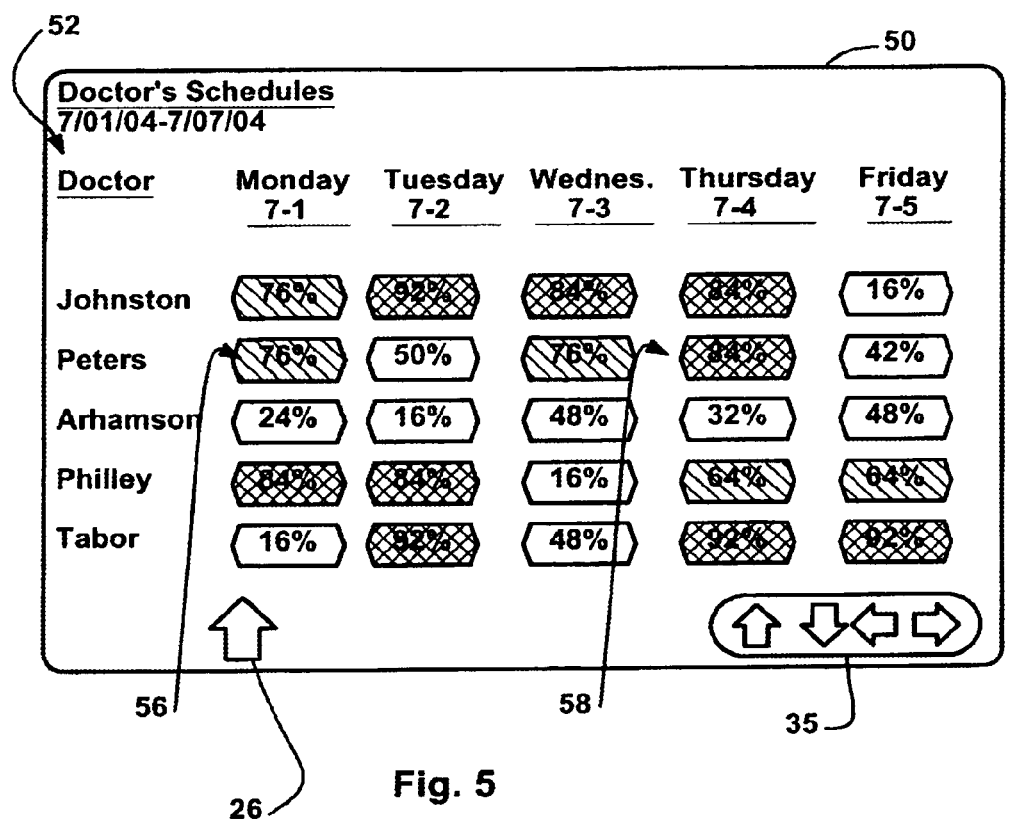
FIG. 5 is a doctor's schedule window illustrating a table that may be provided via the interface of FIG. 1 including optimization indicators for facility doctors and for specific schedule sub-periods.

Referring now to FIG. 5, an exemplary multi-physician, multi-day schedule window 50 is illustrated that includes schedule information as well as optimization indicators for a subset of facility physicians for the July 1-July 5 period. Exemplary window 50 includes a doctors column 52 and five day long sub-period columns corresponding to Monday, July 1, Tuesday, July 2, Wednesday, July 3, Thursday, July 4 and Friday, July 5. Doctor column 52 lists each facility doctor including, consistent with the description above, Dr. Peters. Each of the sub-period columns includes a separate optimization indicator for each one of the doctors in column 52. Consistent with the description above, in at least some embodiments, the optimization indicators are utilization percentages that are obtained from the utilization percentage database 15 as illustrated in FIG. 4. When a scheduler examines window 50 as illustrated in FIG. 5, the scheduler can quickly identify days on which specific physicians have relatively large numbers of open time slots for appointments. In the present example, consistent with information in each of FIGS. 2 and 4, Dr. Peters optimization indicators for Monday through Friday indicate utilization percentages of 76%, 50%, 76%, 84% and 42%, respectively. In addition to the table, window 50 includes a selection cursor 26 for selecting information presented in window 50 and a multifunction scrolling icon 35 for moving about the schedule to observe other schedule sub-periods and associated optimization indicators.

As another example, referring again to FIG. 3, in addition to the scheduling fields and other icons provided on the scheduling screen 220, an optimization indicator 233 may also be provided as part of the screen to remind the scheduler of how optimal it is to schedule another appointment on the associated day. In the FIG. 3 example, consistent with the information in FIG. 2, the optimization indicator for Dr. Peters on Wednesday, July 3 includes a 76% utilization percentage.

Figure 6:
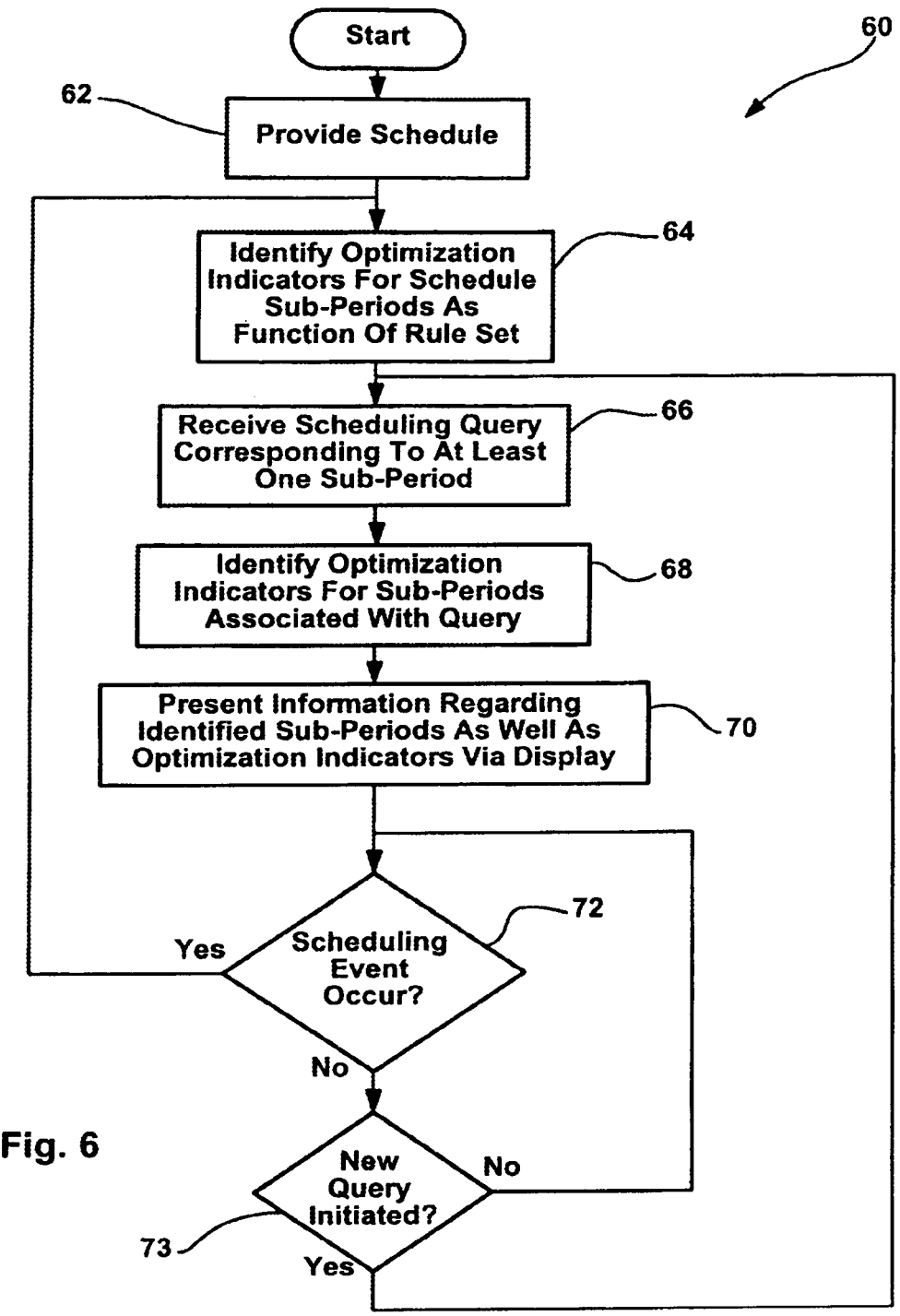
FIG. 6 is a flow chart illustrating a method according to at least some aspects of the present invention.

Referring now to FIG. 6, a method 60 consistent with at least some aspects of the present invention and that may be performed by server 12 (see again FIG. 1) is illustrated. Beginning at block 62, a physician schedule is provided and is stored in database 18. At block 64, server 12 identifies optimization indicators for all schedule sub-periods as a function of the scheduling rule set in database 16. Consistent with the description above, in at least some embodiments, the rule set will simply specify that the optimization indicators are the utilization percentages for working days for each of the facility physicians. At block 66, server 12 receives a scheduling query corresponding to at least one of the schedule sub-periods via interface 14. Here, as described above, the phrase "scheduling query" is used to refer to any activity that causes server 12 to provide scheduling information for one or multiple facility physicians and for one or multiple schedule sub-periods (i.e., working days) to the scheduler via interface 14. Thus, for instance, scheduler activity may cause server 12 to provide scheduling information for multiple days for a single physician as illustrated in FIG. 2, multiple days for multiple physicians as illustrated in FIG. 5 or for a single time slot during an appointment specifying procedure for a single physician as illustrated in FIG. 3. Other schedule presenting screens and windows are contemplated.

After a scheduling query has been received via interface 14, server 12 identifies optimization indicators for the sub-periods associated with a query. For instance, in FIG. 2, where the query causes server 12 to access information associated with the first seven days in July for Dr. Peters, at block 68, server 12 identifies the optimization indicators illustrated in FIG. 2 (i.e., 76%, 50%, 76%, 84%, 42% and 100%). As another example, where the query at block 66 causes server 12 to access information associated with the five days at the beginning of July for all of the facility doctors as illustrated in FIG. 5, at block 68 server 12 identifies optimization indicators for each of the first five days in July for all of the facility physicians. As still one other example, where the query at block 66 causes server 12 to access the scheduling window of FIG. 3 for Dr. Peters 8 AM July 3 appointment, at block 68 server 12 identifies the optimization indicator for Dr. Peters associated with July 3.

Referring again to FIGS. 1 and 6, at block 70, server 12 presents the schedule information associated with the query as well as the optimization indicators via the interface display. Here, for instance, depending on the schedule query at block 66, one of windows 24, 50 or 220, may be presented via the display where optimization indicators are included with the schedule information as illustrated in FIGS. 2, 5 and 3, respectively.

At block 72, server 12 determines whether or not a scheduling event has been initiated via interface 14. Here, referring once again to FIG. 3, after the specifying fields of window 220 have been filled in appropriately and ENTER icon 236 has been selected, a scheduling event occurs to schedule an appointment. Once a scheduling event occurs at block 72 control passes back up to block 64 where server 12 once again identifies optimization indicators for the scheduled sub-periods as a function of the rule set. For instance, in FIG. 3, if ENTER icon 236 were selected to schedule an appointment with Dr. Peters for 8 AM on July 4, the initial 84% utilization percentage for Dr. Peters on July 4 in database 15 (see again FIG. 4) would be changed to 92% at block 64 (i.e., 8% would be added to the initial value). At block 72, if a scheduling event does not occur, control passes to block 73 where server 12 monitors for a new query. Until a new query is received or an appointment is scheduled, control loops through decision blocks 72 and 73. When a query is received at block 73, control passes back up the block 66 where the process described above is repeated.

In at least some embodiments it is contemplated that relatively more informative optimization indicators may be provided by server 12 to more strongly suggest specific scheduled time slots for appointments. For example, in at least some embodiments it is contemplated that facility scheduling rules may specify that appointments can be made during any work day where the current utilization percentage for a specific physician is less than 60%, preferably should not be made if the utilization percentage is between 60% and 80% and, only under extenuating circumstances, should be made if the utilization percentage is 80% or greater. In this case, in addition to providing utilization percentages as optimization indicators, in at least some cases, it is contemplated that a visual queue may also be provided that clearly indicates whether or not facility scheduling rules encourage or discourage appointment scheduling during specific days. For example, consistent with the exemplary rules above, where a utilization percentage for a specific day is less than 60%, a green screen element, icon or the like may be provided along with the utilization percentage for a specific day, where the utilization percentage is within a range of 60% to 80%, the icon or element may be yellow and where the utilization percentage is greater than 80%, the icon or element may be red.

Referring once again to FIG. 2, icons or elements having visually distinct characteristics are provided as part of each of the optimization indicators. For example, an icon 32 is provided as part of the optimization indicator for Dr. Peters for the Monday July 1 time slot, an icon 29 is provided which is associated with the Tuesday July 2 time slot, an icon 34 is provided as part of the optimization indicator corresponding to Thursday July 4, etc. In FIG. 2 as well as in other figures, yellow icons are indicated via left to right downward cross-hatching, green icons are indicated by no cross-hatching (i.e., are white as illustrated) and red icons are indicated by double cross-hatching. Thus, for instance, in FIG. 2, icon 32 corresponds to a yellow icon, icon 29 corresponds to a green icon and icon 34 corresponds to a red icon. It should be appreciated that, when observing a schedule window 24 and, specifically, the optimization indicators, the different visual representations enable a scheduler to quickly identify optimal days on which appointments should be scheduled and other day on which scheduling of additional appointments is discouraged.

Referring again to FIG. 5, icons similar to those described above with respect to FIG. 2 are provided, one for each of the utilization percentages illustrated where color coding is usable to quickly and easily identify days on which appointments with specific physicians are encouraged and days on which appointments with those physicians are discouraged given the scheduling rules adopted by the facility. Similarly, referring again to FIG. 3, optimization indicator icon 233 is color coded to clearly suggest whether or not scheduling an additional appointment on July 3 for Dr. Peters is encouraged or discouraged.

Figure 7:
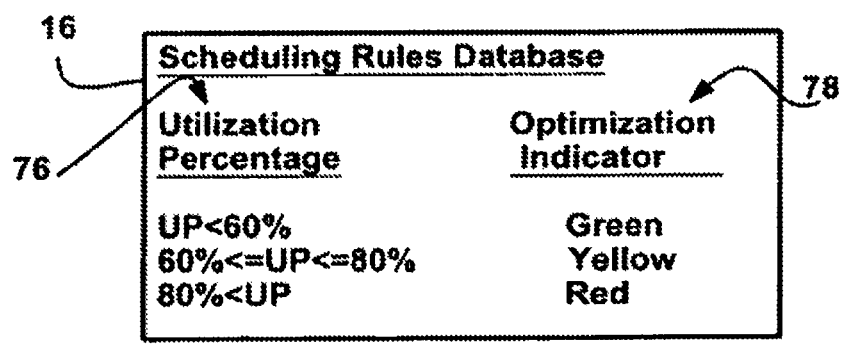
FIG. 7 is an exemplary scheduling rules database that may be employed by the server of FIG. 1.

Referring now to FIG. 7, an exemplary scheduling rules database 16 is illustrated which includes a utilization percentage column 76 and an optimization indicator column 78. The utilization percentage column, as its label implies, specifies specific utilization percentages. Consistent with the example above, three different utilization percentages are specified in column 76 including less than 60%, within the 60% to 80% range, and greater than 80%. Optimization indicator column 78 indicates a different color for each one of the utilization percentages in column 76. For the percentage less than 60%, column 78 indicates that the optimization indicator should be colored green. Similarly, for each of the utilization percentage ranges of 60% to 80% and greater than 80%, column 78 indicates that the optimization indicators should be colored yellow and red, respectively.

Referring once again to FIG. 6, method 60 can be used with the scheduling rules database 16 described in FIG. 7 to perform the optimal scheduling suggesting function, the only difference being that when the optimization indicators are identified, in addition to identifying the utilization percentages, server 12 identifies the color of the icon or icons that will be displayed along with the schedule information corresponding to the query.

In at least some embodiments it is contemplated that the colors of the optimization indicators or icons may, in addition to being a function of the utilization percentages, also be a function of other schedule characteristics. For example, in at least some cases it is contemplated that, while appointment scheduling may be discouraged unless extenuating circumstances exist when a utilization percentage is greater than 80%, when the day associated with the relatively high utilization percentage occurs, appointments may be encouraged to ensure that physician schedules are generally filled. As another example, while appointments on days having utilization percentages in the 60% to 80% range may be generally discouraged, when the day associated with the relatively high utilization percentage is only 1 or 2 days away, appointments may be encouraged so as to fill up physician schedules.

Figure 8:
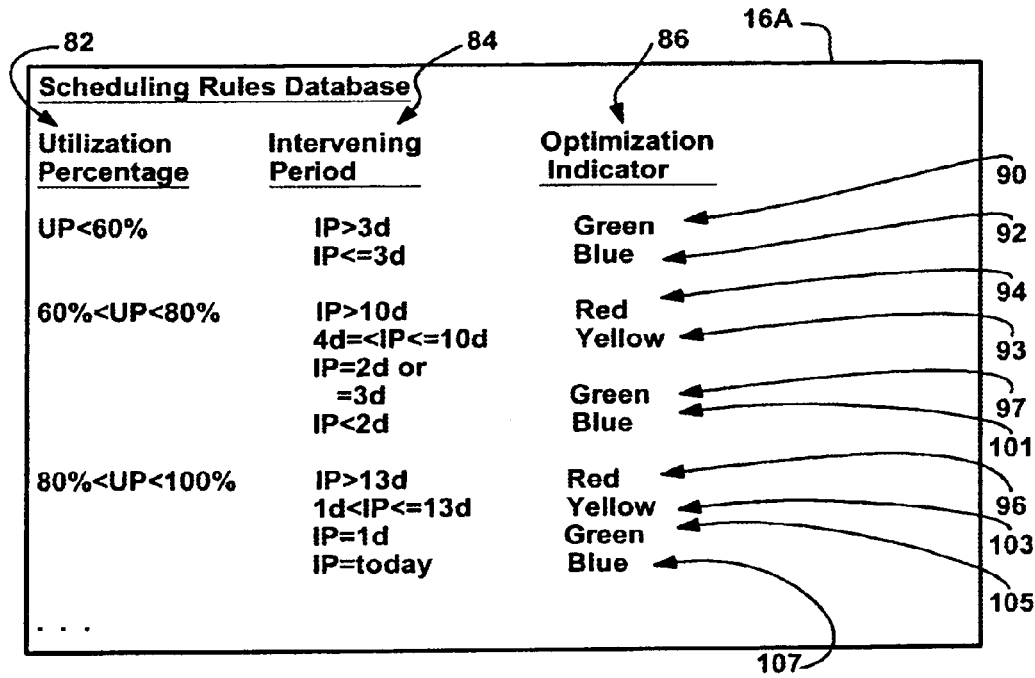
FIG. 8 is similar to FIG. 7, albeit illustrating a more complex scheduling rules database.

Referring now to FIG. 8, a more complex scheduling rules database 16A is illustrated which includes a utilization percentage column 82, an intervening period IP column 84 and an optimization indicator column 86. Utilization percentage column 82 lists three separate utilization percentages including less than 60%, within the 60% to 80% range, and greater than 80%. Intervening period column 84 includes at least two intervening periods for each of the utilization percentages in column 82. In column 84, a "d" indicates a period corresponding to a day where number qualifiers prior to a "d" indicate a number of days. Thus, "3d" indicates a three day intervening period with respect to the current date.

Referring still to FIG. 8, optimization indicator column 86 indicates a specific color for each one of the intervening periods in column 84. Thus, database 16A specifies at least two intervening period-optimization indicator color pairs for each of the utilization percentages. For example, database 16A specifies two period-color pairs for the less than 60% utilization percentage including a green color 90 associated with an intervening period of four or more days and a blue color 92 associated with an intervening period of three or less days. Similarly, database 16A specifies four period-color pairs for utilization percentages in the 60% to 80% range including a red color 94 associated with an intervening period of 11 or more days, a yellow color 93 associated with an intervening period of between four and ten days, a green color 97 associated with an intervening period of either two or three days and a blue color 101 associated with an intervening period of one day and specifies four period-color pairs for utilization percentages greater than 80% including red 96, yellow 103, green 105 and blue 107 colors associated with intervening periods of fourteen or more days, between two and thirteen days, one day and zero days, respectively.

Hereinafter the period-color pairs and corresponding utilization percentages will be referred to as rules and identified by one of the numbers that appears along the right edge of FIG. 8. Thus, number 90 will be referred to as a rule that specifies that when the utilization percentage is less than 60% and the intervening period is four or more days, the optimization indicator should be green while rule 92 specifies that when the utilization percentage is less than 60% and the intervening period is three or less days, the optimization indicator should be blue. In the present example, it is contemplated that a blue icon will be used to strongly encourage the scheduler to schedule any appointments that can be made during the associated work day.

Referring still to FIG. 8 and specifically to the 60% to 80% range, according to rule 94, when the intervening period between a current day and a scheduled day is greater than 10 days, the color of the optimization indicator or icon is red thereby discouraging a scheduler from scheduling appointments on that particular day. However, when the intervening period is between four and 10 days and the utilization percentage is in the 60% to 80% range, rule 93 specifies that the optimization indicator or icon color is changed from red to yellow indicating that, while appointment scheduling during the associated day is still discouraged, it is no longer strongly discouraged. When the intervening period is two or three days away and the utilization percentage is in the 60% to 80% range, rule 97 specifies that the optimization indicator or icon color is changed to green thereby encouraging scheduling during the associated day. Finally, when the intervening period is less than two days away and the utilization percentage is in the 60% to 80% range, rule 101 specifies that the optimization indicator or icon color is changed from green to blue strongly encouraging appointment scheduling the corresponding day.

Similarly, referring to the utilization percentage range greater than 80%, when the intervening period is fourteen days or greater, rule 96 specifies that the optimization indicator should be red to strongly discourage scheduling, when the intervening period is between two and thirteen days, rule 103 specifies that the optimization indicator should be yellow to discourage scheduling, when the intervening period is only one day, rule 105 specifies that the optimization indicator should be green to encourage scheduling and when a schedule time occurs on the current day, rule 107 specifies that the optimization indicator should be blue to strongly encourage scheduling.

Figure 9:
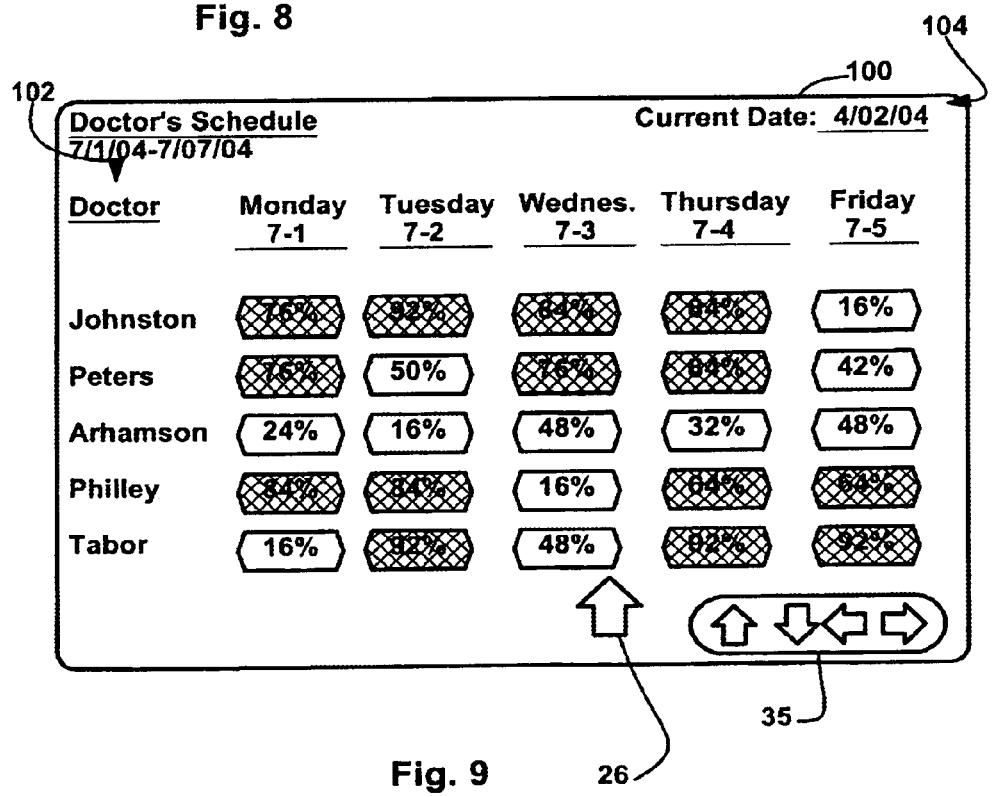
FIG. 9 is a doctors schedule window similar to the view of FIG. 5 albeit including a different set of optimization indicators associated with a long intervening period and consistent with the rules specified in FIG. 8.

Referring now to FIG. 9, a window 100 similar to the window 50 of FIG. 5 is illustrated which includes a current date field 104 that indicates a current date of Apr. 2, 2004 which is several months and, in the context of the present example, more than fourteen days prior to the portion of the schedule presented by window 50 that corresponds to July 1 through July 5. Consistent with the rules database 16A of FIG. 8 and specifically rules 90, 94 and 96, all of the optimization indicators corresponding to utilization percentages under 60% are illustrated as being green (i.e., without cross-hatching) while each of the optimization indicators associated with utilization percentages greater than 60% is shown as being red (i.e., double cross-hatched). Here, as in FIG. 5, a scheduler can visually analyze the information in FIG. 9 to quickly identify days for each physician on which additional appointment scheduling is encouraged and discouraged.

Figure 10:
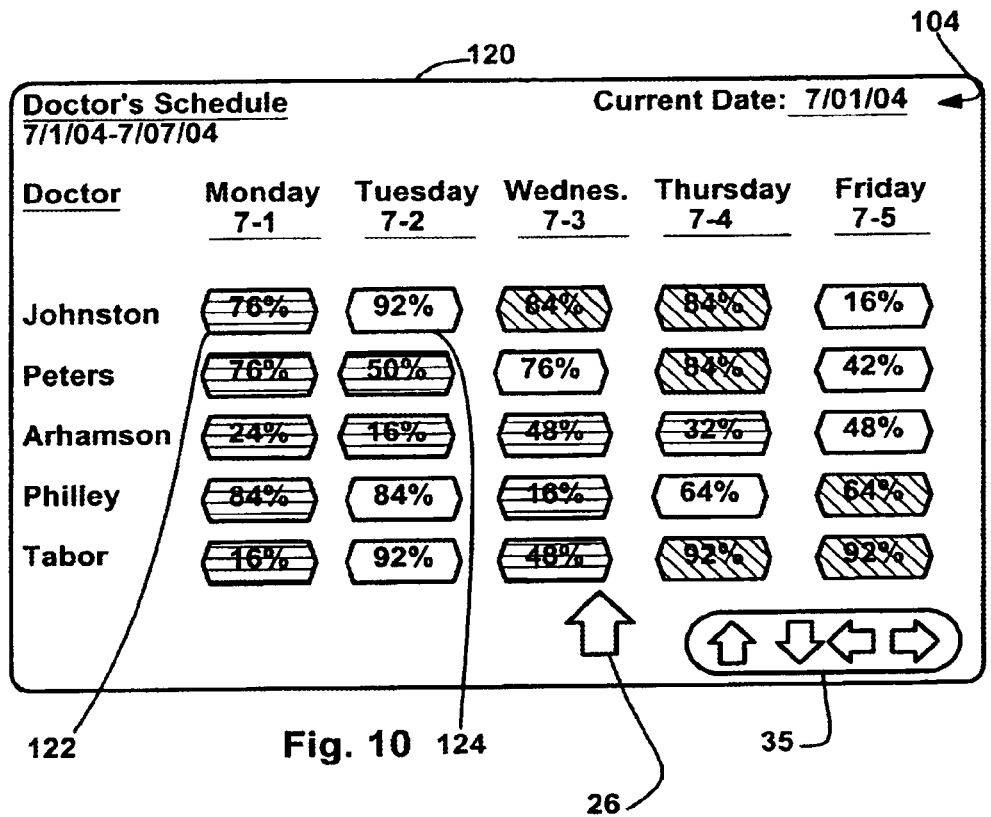
FIG. 10 is a doctors schedule window similar to the view of FIG. 5 albeit including a different set of optimization indicators associated with a short intervening period and consistent with the rules specified in FIG. 8.

Referring also to FIG. 10, another doctor's schedule window 120 similar to the windows illustrated in FIG. 9 is shown. In FIG. 10 blue colored optimization indicators or icons are indicated by horizontal cross-hatching. Thus, for example, icon 122 that includes horizontal cross-hatching is blue.

In FIG. 10, the current date in date field 104 is indicated as Jul. 1, 2004. Consistent with the rules specified by database 16A in FIG. 8 and specifically rules 92, 97 and 107, because the current date is Monday July 1, all of the optimization indicators in the Monday July 1 column are blue even though some of the utilization percentages are relatively high. Similarly, consistent with rule number 92, each of the optimization indicators associated with a utilization percentage less than 60% in the Tuesday July 2 column are blue. Consistent with rule 103, each of the optimization indicators associated with a utilization percentage greater than 80% in the Tuesday July 2 column is green. Consistent with rules 92, 97 and 103, each of the optimization indicators associated with utilization percentages less than 60% and in the 60% to 80% range and above 80% in each of the Wednesday, July 3 and Thursday, July 4 columns are blue, green and yellow, respectively. Consistent with rules 90, 93 and 103, each of the optimization indicators associated with utilization percentages less than 60%, in the 60% to 80% range and greater than 80% in the Friday, July 5 column are green, yellow and yellow, respectively. Once again, the optimization indicators provided via window 120 provide valuable optimization information to a scheduler.

Figure 11:
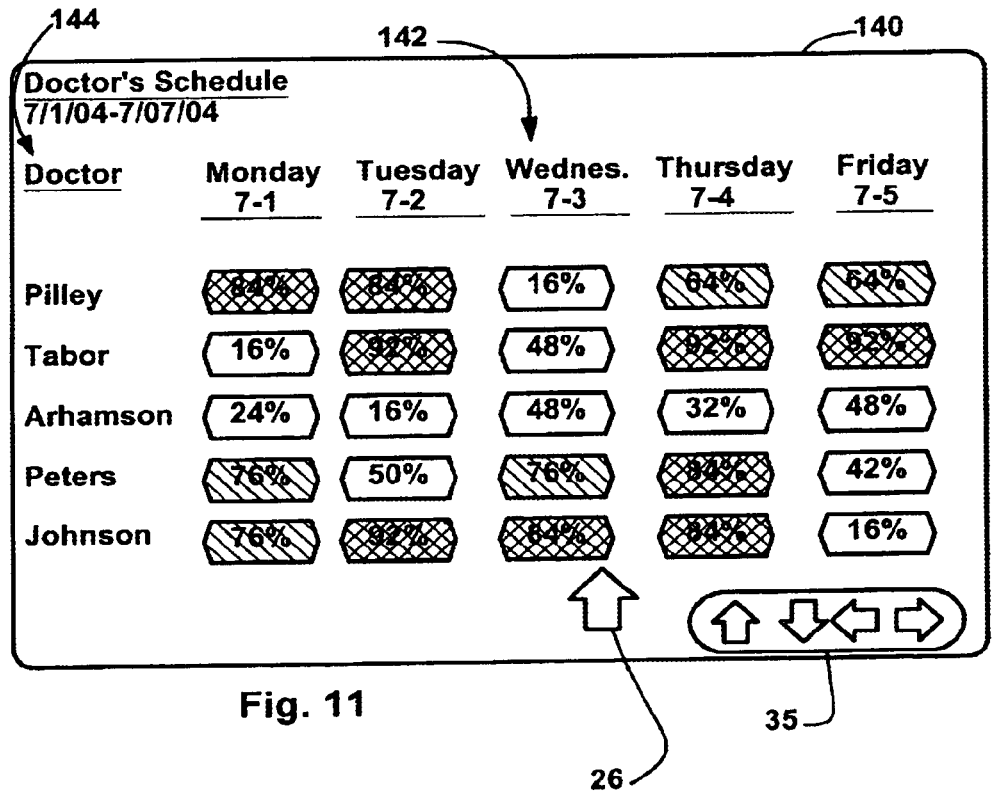
FIG. 11 is a doctors schedule window view similar to the view of FIG. 5 albeit where the physician list and associated optimization indicators have been reordered as a function of relative utilization percentages on one of the working days.

Various other information manipulating tools are contemplated by the present invention to help a scheduler examine schedule information and make optimized scheduling decisions. For example, referring once again to FIG. 5, in at least some embodiments it is contemplated that when a doctor's schedule window 50 is provided via interface 14, cursor 26 may be useable to select displayed information and thereby rearrange the schedule information and optimization indicators in different ways. For instance, if cursor 26 is used to select the text corresponding to Wednesday, July 3 at the top of the illustrated table, server 12 may be programmed to reshuffle the physicians in column 52 as well as the optimization indicators associated therewith so that the physicians are presented in the table with the physicians that have the most open time slots on Wednesday, July 3, at the top of the table and those that have the least open time slots on July 3 at the bottom of the table. To this end, see window 140 in FIG. 11 where the physicians in doctor column 144 have been reshuffled as a function of relative utilization percentages in column 142 corresponding to Wednesday, July 3. Thus, Dr. Philly who has a 16% utilization percentage in column 142 is at the top of the table followed by Dr. Tabor with a 48% utilization percentage and so on.

While relatively simple scheduling rules have been described above, it should be appreciated that more complex rules are contemplated that take into account other schedule characteristics in addition to utilization percentage and intervening period. For example, where two physicians that generally provide similar services work at a single facility and one of the physicians has a schedule that is routinely within the 60% to 80% utilization percentage range or higher while the other physician is routinely below 60% scheduled utilization, server 12 may be programmed to suggest appointment scheduling with the physician that is less busy. Thus, the scheduling rules may cause server 12 to take in to account multiple physician schedules when identifying optimization indicators.

Similarly, the scheduling rules may cause server 12 to take in to account utilization percentages of temporally proximate days or other sub-periods when identifying an optimization indicator for a specific day or sub-period. For instance, assume that the scheduling rules generally provide a yellow optimization indicator when a utilization percentage for a particular day is in the 60% to 80% range for Dr. Peters. Also assume that, during a two week period, the utilization percentages for all of the working days are within the 80% to 100% range for Dr. Peters except for one of the days which is associated with the 60% to 80% utilization percentage range. Here, because there are no temporally proximate good options for scheduling an appointment, the scheduling rules may make an exception such that the optimization indicator for the day corresponding to the 60% to 80% utilization percentage range will be colored green instead of yellow.

In addition to or instead of providing optimization indicators corresponding to work days, other scheduling optimization information may be provided by server 12. For example, while appointment scheduling during a day associated with a 50% utilization percentage may be encouraged, there may be optimal time slots during the day for scheduling an appointment. For instance, where a day includes twelve time slots and five are open in the morning while only 1 is open in the afternoon, it will typically be advantageous to schedule appointments during one of the open morning time slots as opposed to the single open afternoon time slot. Here, by scheduling in the morning instead of in the afternoon, the afternoon slot will remain open for later emergency appointments or, if not filled, to reduce the physician's workload in the afternoon. In this case, server 12 may be programmed to visually distinguish optimal time slots for appointment scheduling in addition to visually distinguishing optimal days or other sub-periods for appointment scheduling.

Figure 12:
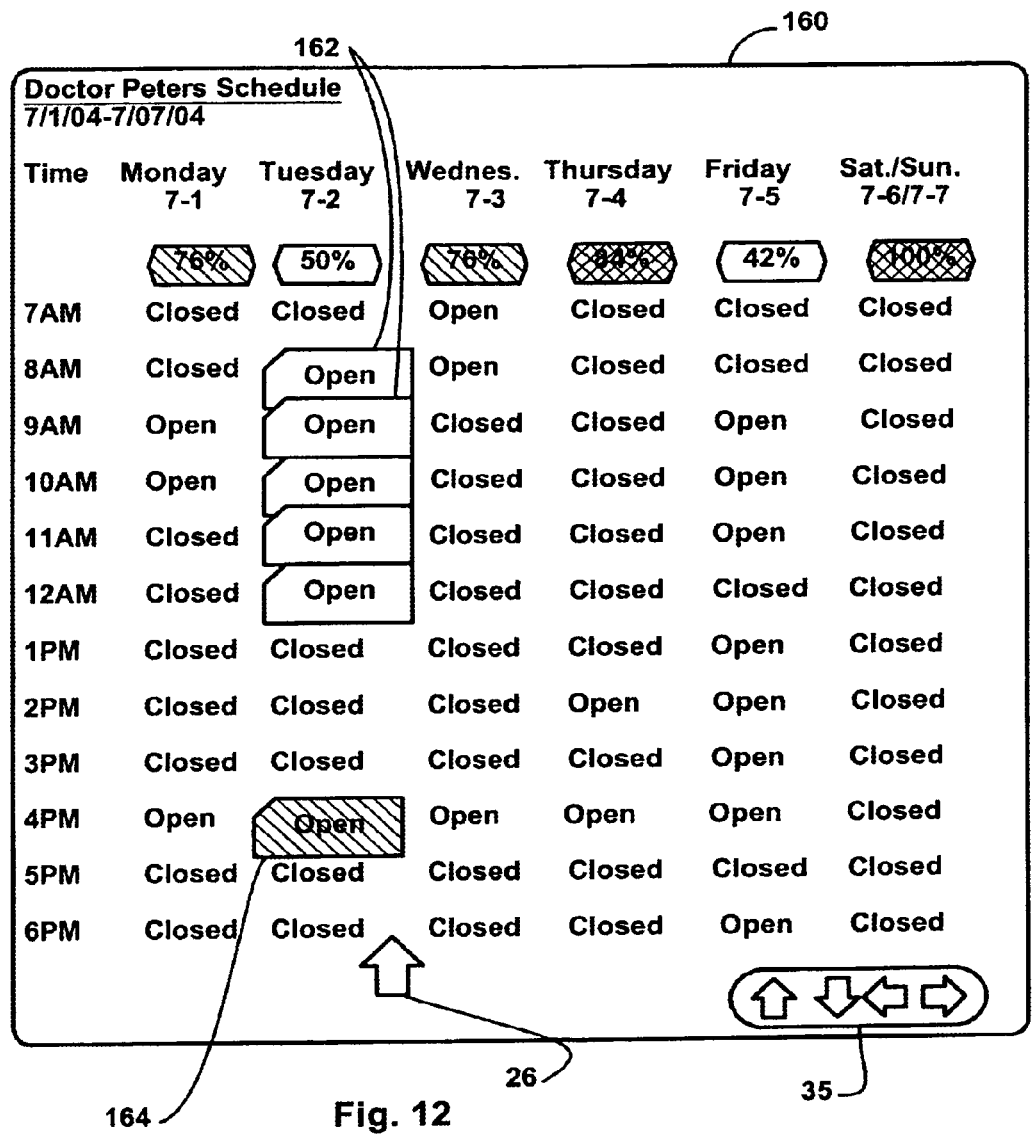
FIG. 12 is a doctors schedule window similar to the window of FIG. 2 that includes supplemental optimization indicators that suggest preferential time slots within a given working day.

Referring now to FIG. 12, a schedule window 160 similar to window 24 in FIG. 2 is illustrate where additional optimization indicators are included. The additional optimization indicators are shown as icons spatially corresponding to several of the "open" status designations in the Tuesday, July 2 column. Two of the additional optimization indicators are collectively identified by numeral 162 while a third is identified by numeral 164. Consistent with the above example, five open time slots exist in the morning of July 2, (i.e., at 8, 9, 10, 11 and 12 AM) and only one open time slot at 4 PM exists in the afternoon. To encourage scheduling of appointments during the morning time slots and discourage scheduling during the open afternoon time slot, the optimization indicators 162 associated with each one of the morning time slots is shown as being colored green (i.e., no cross-hatches) while the optimization indicator 164 associated with the open afternoon time slot is shown as being colored yellow (i.e., includes left to right downward cross-hatches). Here, once again, clearly a scheduler observing window 160 could quickly identify optimal time slots for scheduling an appointment and other time slots that are discouraged given facility scheduling rules.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

For example, while utilization percentages are provided above in at least some embodiments as optimization indicators or parts thereof, in some embodiments optimization indicators may not include utilization percentages or indeed may be based on one or more other schedule factors. For instance, in some cases optimization indicators may simply include color coded icons as described above which, while based at least in part on utilization percentages, would not necessarily include presentation of numeric percentages. As another instance, instead of basing optimization indicators on utilization percentages the indicators may be based at least in part on the number of closed or open time slots in a sub-period (e.g., in a day). For instance, when 10 of 12 time slots are filled, a red optimization indicator may be provided. As still one other instance, instead of determining utilization percentages and expressing those percentages, availability percentages (i.e., the percentage of available schedule time) may be identified and used to suggest optimal scheduling time slots, fractions (e.g., 7/12 to indicate that seven of 12 slots are open) or other suitable indicators may be provided.

In addition, while the invention is generally described above in the context of a system wherein utilization percentages are determined on a day by day basis, other sub-periods are contemplated such as weeks, half days, quarter days, etc.

Moreover, in addition to simply suggesting optimal schedule sub-periods and/or time slots for scheduling new appointments, it is contemplated that at least some systems may restrict non-optimal scheduling under at least some circumstances. For instance, most emergencies will require almost immediate attention (e.g., attention within two days) and therefore, in at least some cases where a utilization percentage is greater than 80% and an intervening period is more than two days, the rules may not allow scheduling of new appointments during days associated with the greater than 80% percentage range.

Furthermore, at least some of the above inventions and aspects will be useable in the context of other schedule scanning procedures/processes. For instance, a scheduler may specify a specific doctor and maximum utilization percentage causing the server to identify at least a subset of time slots that fit the query. As another instance, server 12 may be programmed to identify only highly optimal schedule times unless the scheduler indicates that other less optimal times should also be identified.

In addition, optimization indicators may be based on other information in addition to current utilization percentages such as the current sub-period utilization percentages of sub-periods temporally proximate other sub-periods, distribution of current appointments during a sub-period, multiple physician schedules, and so on.

In at least some cases the optimization indicator may also be identified at least in part as a function of a specified appointment duration for an appointment to be scheduled. In this regard, it has been recognized that whether or not an appointment should be scheduled during open schedule sub-periods may be a function of expected appointment duration. For instance, where seven hours of a ten hour day for a particular physician are already scheduled and the physician does not want to book more than 8 hours in any given day, where a first appointment is expected to be less than one hour in duration, it may be prudent to schedule the appointment. However, where a second appointment is expected to require 2 hours, the second appointment should not be scheduled as the second appointment would overbook the physician's schedule.

Consistent with the above example, in at least some cases, it is contemplated that after an expected appointment duration or some other information (i.e., appointment type or expected activity) from which expected appointment duration can be determined is specified by a scheduler via an input interface, the inventive system may be programmed to identify possible utilization percentages as a function of current utilization percentages and the expected appointment duration and may then provide optimization indicators as a function of the possible utilization percentages. In the above example where the physician's schedule is already 70% full and an appointment to be made is expected to require one hour, the system would identify an 80% (i.e., 8 out of 10 hours) possible utilization percentage and an appropriate optimization indicator that reflects 80% would be provided—e.g., an indicator that indicates that the appointment can be made during the associated sub-period. In the alternative, where the appointment to be scheduled is expected to require two hours, the system would identify a 90% (i.e., 9 out of 10 hours) possible utilization percentage and an appropriate optimization indicator that reflects 90% would be provided—e.g., an indicator that indicates that the appointment should not be made during the associated sub-period.

Moreover, where a physician specifies a specific limit to how full the schedule corresponding to a day can be, the utilization percentage may be specified as a percentage of the total amount of time that can be scheduled for a specific day. For instance, while a physician may work for 10 hours in a day, the physician may reserve two hours during each 10 hour work day during which appointments will not be taken under any circumstances. Here, the utilization percentage may be based on the 8 hours of possible scheduling time instead of the total 10 hours. Thus, for instance, where 6 hours are currently scheduled, instead of indicating a 60% utilization rate, the system may be programmed to indicate a 75% utilization rate (i.e., 6/8=0.75).

Moreover, in at least some cases, optimization indicators may be identified as a function of both utilization rates or percentages and related currently scheduled appointments or related appointments to be scheduled or both currently scheduled and to be scheduled appointments. For instance, where a client intends to schedule two appointments and would like to schedule those two appointments temporally consecutively with two different physicians at the same facility, the utilization percentage ranges associated with specific optimization indicators may be different than in the case where a single appointment is being scheduled as the likelihood of locating temporally consecutive appointment times in the two physician schedules will be less in most cases. For instance, a first physician may have a general rule that the physician prefers not to fill a days schedule more than 70% full but may allow filling up to 85% to accommodate clients that already have scheduled and temporally proximate appointments or that want to schedule another temporally proximate appointment. Here, for instance, where the first physician's schedule is already 75% booked on a Monday on which a client already has an appointment scheduled with a second physician and the client attempts to schedule a second appointment with the first physician on the overbooked Monday, the system may encourage scheduling of the appointment on the Monday up to the 85% cutoff value. Thus, for instance, the system may provide a green icon indicating an optimal scheduling period despite the fact that, if the patient did not already have a scheduled appointment with the second physician, the icon may have been red or yellow. Similar rules may be specified and applied for multiple appointments that have yet to be made for a single client or for appointments that are to be made or have been made for related clients (i.e., a mother and her child that each require temporally proximate appointments).

In addition, the present invention is meant to be used in more complex systems where multiple layers of optimization are contemplated. For instance, in a facility that includes ten physicians and a limited administrative staff, in addition to each of the physicians having a schedule and associated optimization indicators, the facility as a whole may have a schedule and associated optimization indicators. For example, it may be that the administrative staff is capable of comfortably processing only 170 appointments in a given day. Here, where each physician can see a maximum of 20 clients in a given day for a total of 200 appointments (i.e., 10 physicians×20 appointments/day=200 appointments/day), the facility can only process 85% of the maximum number of appointments. Thus, in addition to tracking physician schedules and optimization indicators, the system may also track the facility schedule and indicators and may restrict or limit appointment scheduling via presentation of indicators to the scheduler.

Figure 13:
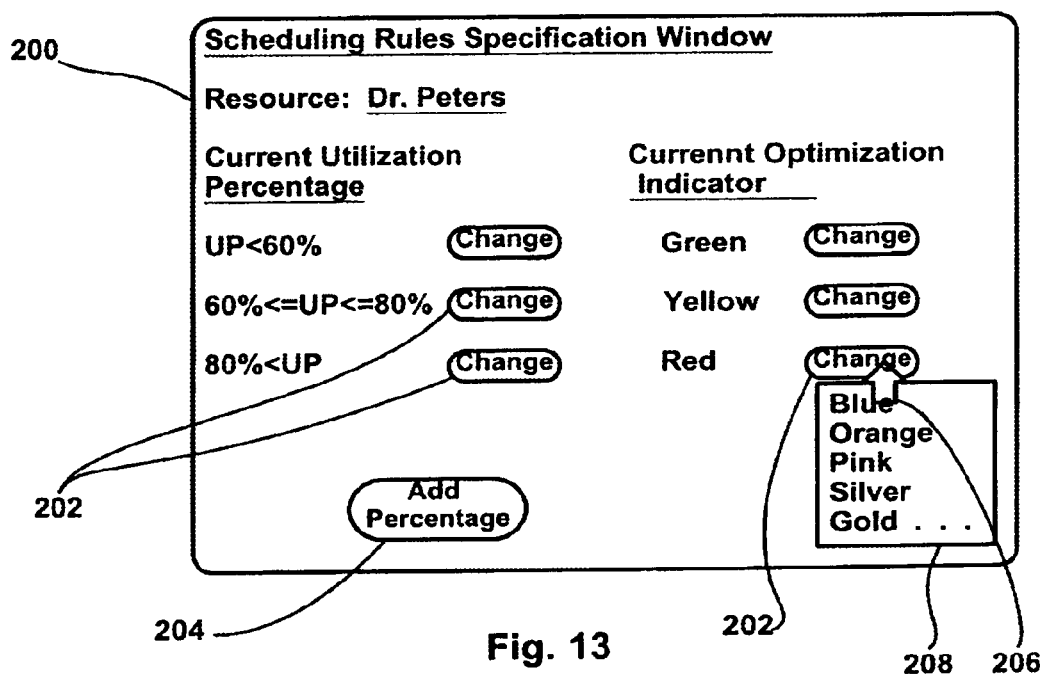
FIG. 13 is a scheduling rules specification window consistent with at least some aspects of the present invention.

Moreover, systems are contemplated wherein optimization indicators and associated utilization percentage ranges are set for entire facilities, for separate facility departments on a department by department basis or indeed where the percentage ranges are set on a physician/resource by physician/resource basis and where the ranges and indicators can be personalized. To this end, referring to FIG. 13, a screen shot 200 that may be provided via server 12 for use in altering optimization indicators and/or percent ranges associated therewith for Dr. Peters is illustrated. The exemplary shot includes screen selectable "CHANGE" icons, three of which are collectively identified by numeral 202, one for each of the currently specified percentage ranges, and one for each of the optimization indicator colors associated therewith, an "ADD PERCENTAGE" icon 204 and a drop down menu 208. Cursor 206 is moveable about the screen to select screen icons. To alter one of the existing percentage ranges the cursor 206 can be used to select an associated CHANGE icons 202. Similarly, to change one of the optimization identifier colors, cursor 206 can be used to select an associated icon 202. In the illustrated example, icon 202 associated with the red optimization indicator is selected and drop down menu 208 has been provided from which a different color may be selected to replace the red color. To add an unspecified range, icon 204 may be selected. Other screen shots are contemplated that would further instruct a system administrator with respect to changing settings.

While systems are contemplated where optimization indicators and utilization percentages may be customized for departments or for specific resources, in at least some cases it is contemplated that certain color and range relationships could be enforced across all departments and resources. For instance, red may always indicate that scheduling for an appointment is disallowed irrespective of the ranges that each department or resource associates with the red color while green may always indicate that scheduling is encouraged. For example, while first and second departments may prohibit scheduling when schedules are 75% and 85% full, respectively, both may be required to use the same red color as part of the optimization indicator to indicate the restriction. By enforcing rules across a facility, schedulers that use the resources have an easier time of understanding the meanings of the different optimization indicators.

Furthermore, in the claims that follow, unless indicated otherwise, the term resource is used in a very broad sense to refer to any resource that could be used or employed during an appointment including but not limited physicians, nurses, medical equipment such as imaging systems, surgical systems and other diagnostic systems, IVs, beds, rooms, etc. Similarly, in the claims, unless indicated otherwise, the term "scheduler" will be used in a broad sense to refer to any person using an interface in an attempt to obtain scheduling information for resources. Thus, for instance, the term scheduler includes employees or contractees of a medical facility that are specifically hired to communicate with clients and schedule appointments, includes clients themselves that may use the Internet or the like to obtain scheduling information or to schedule appointments using a PC or the like, includes physicians and/or nurses, etc.

To apprise the public of the scope of this invention, the following claims are made:

What is claimed is:

1. A method for use with a processor, a database and an interface including a display screen, the database including resource schedule information associated with utilization of time for at least one medical resource, the method for aiding a scheduler responsible for scheduling the medical resource to optimally schedule new requests for the resource's time, the method comprising the steps of:

running the processor to perform the steps of:
retrieving a rule defining at least three optimization indicators each corresponding to a relative degree of optimization associated with scheduling the medical resource during a future sub-period during which the medical resource is available for scheduling, each of the optimization indicators corresponding at least in part to a utilization value of the medical resource calculated as a total sub-portion of the future time period during which the medical resource is currently scheduled;
scheduling first and second appointments during first and second sub-portions of a first future sub-period during which the medical resource is available for scheduling on the resource schedule, respectively;
scheduling first and second appointments during first and second sub-portions of a second future sub-period during which the medical resource is available for scheduling on the resource schedule, respectively;
identifying a first utilization value for the first future sub-period wherein the first utilization value is indicative of a total sub-portion of the first future sub-period during which the medical resource is currently scheduled;
identifying a second utilization value for the second future sub-period wherein the second utilization value is indicative of a total sub-portion of the second future sub-period during which the medical resource is currently scheduled;
identifying the optimization indicator associated with scheduling the medical resource during at least a sub-portion of the first future sub-period;
identifying the optimization indicator associated with scheduling the medical resource during at least a sub-portion of the second future sub-period; and
simultaneously presenting the optimization indicators associated with scheduling the medical resource during at least a sub-portion of the first future sub-period and the optimization indicator associated with scheduling the medical resource during at least a sub-portion of the second future sub-period via the display, wherein the display enables the scheduler to directly compare the optimization indicators corresponding to the sub-portions of the first and second future sub-periods, respectively, to select a time for another appointment for the medical resource that enables optimization of use of the medical resource.

2. The method of claim 1 wherein the utilization value is a utilization percentage of the at least one sub-period.

3. The method of claim 1 wherein the scheduler is affiliated with an entity that controls the medical resource, the method further including receiving a scheduling request from a client attempting to identify availability of the medical resource for an appointment to be scheduled.

4. The method of claim 1 wherein the scheduler is a client attempting to identify availability of the medical resource for an appointment that the client desires to schedule and wherein the step of presenting the optimization indicator includes providing a network link between the processor and the interface and presenting the optimization indicator remotely to the client.

5. The method of claim 1 wherein the medical resource is a medical service provider and wherein the step of identifying a utilization value includes identifying the percent utilization of the provider's time over the at least one sub-period.

6. The method of claim 5 wherein the step of presenting an optimization indicator includes presenting a visually distinct indicator where the distinction is a function of the value of the utilization percentage.

7. The method of claim 6 wherein the step of presenting an optimization indicator includes presenting a color coded icon wherein the color of the icon depends at least in part on the utilization percentage.

8. The method of claim 7 wherein there are a plurality of different percentage ranges and wherein the color of each icon depends at least in part on the range that includes an associated utilization percentage.

9. The method of claim 8 wherein the ranges and the colors are selectable by the scheduler.

10. The method of claim 7 wherein the step of presenting an optimization indicator also includes indicating the utilization percentage via a percentage number.

11. The method of claim 10 wherein the percentage number is placed within the color coded icon.

12. The method of claim 1 wherein the utilization value is greater than zero percent and less than 100 percent.

13. The method of claim 1 wherein the optimization indicators each indicate a relative degree of optimization associated with scheduling the medical resource during at least a sub-portion of the first future sub-period that is not currently scheduled.

14. An apparatus for aiding a scheduler responsible for scheduling at least one resource to optimally schedule new requests for the resource's time, the apparatus comprising:
    an interface;
    a display screen;
    a database including resource schedule information associated with utilization of time for at least one resource that may be scheduled for use over a period including several sub-periods;
    and
    a processor programmed to perform the steps of:
    retrieving a rule defining at least three optimization indicators each corresponding to a relative degree of optimization associated with scheduling the medical resource during a future sub-period during which the medical resource is available for scheduling, each of the optimization indicators corresponding at least in part to a utilization value of the medical resource calculated as a total sub-portion of the future time period during which the medical resource is currently scheduled;
    scheduling first and second appointments during first and second sub-portions of a first future sub-period on the resource schedule, respectively;
    scheduling first and second appointments during first and second sub-portions of a second future sub-period on the resource schedule, respectively;
    identifying a first utilization value for the first future sub-period wherein the first utilization value is indicative of a total sub-portion of the first future sub-period during which the medical resource is currently scheduled;
    identifying a second utilization value for the second future sub-period wherein the second utilization value is indicative of a total sub-portion of the second future sub-period during which the medical resource is currently scheduled;
    identifying the optimization indicator associated with scheduling the medical resource during at least a sub-portion of the first future sub-period;
    identifying the optimization indicator associated with scheduling the medical resource during at least a sub-portion of the second future sub-period; and
    simultaneously presenting the optimization indicators associated with scheduling the medical resource during at least a sub-portion of the first future sub-period and the optimization indicator associated with scheduling the medical resource during at least a sub-portion of the second future sub-period via the display, wherein the display enables the scheduler to directly compare the optimization indicators corresponding to the sub-portions of the first and second future sub-periods, respectively, to select a time for another appointment for the medical resource that enables optimization of use of the medical resource.

15. The apparatus of claim 14 wherein the utilization values are utilization percentages of the sub-periods.

16. The apparatus of claim 14 wherein the scheduler is a client attempting to identify availability of the resource for an appointment that the client desires to schedule, the apparatus further including a network that links the interface and display to the processor, the processor programmed to perform the step of presenting the optimization indicator by linking to the interface via the network and presenting the optimization indicator remotely to the client.

17. The apparatus of claim 14 wherein the utilization value is greater than zero percent and less than 100 percent.

18. The apparatus of claim 14 wherein the utilization value is a utilization percentage of the at least one sub-period.

19. The apparatus of claim 14 wherein the scheduler is affiliated with an entity that controls the medical resource, the method further including receiving a scheduling request from a client attempting to identify availability of the medical resource for an appointment to be scheduled.

20. The apparatus of claim 14 wherein the scheduler is a client attempting to identify availability of the medical resource for an appointment that the client desires to schedule and wherein the step of presenting the optimization indicator includes providing a network link between the processor and the interface and presenting the optimization indicator remotely to the client.

21. The apparatus of claim 14 wherein the medical resource is a medical service provider and wherein the step of identifying a utilization value includes identifying the percent utilization of the provider's time over the at least one sub-period.

22. The apparatus of claim 14 wherein the optimization indicator comprises a visually distinct indicator where the distinction is a function of the value of the utilization percentage.

23. The apparatus of claim 14 wherein the optimization indicator comprises color coded icon wherein the color of the icon depends at least in part on the utilization percentage.

24. The apparatus of claim 14 comprising a plurality of different percentage ranges and wherein the color of each icon depends at least in part on the range that includes an associated utilization percentage.

25. The apparatus of claim 14 wherein the ranges and the colors are selectable by the scheduler.

26. The apparatus of claim 14 wherein the optimization indicator also includes indicating the utilization percentage via a percentage number.

27. The apparatus of claim 14 wherein the percentage number is placed within the color coded icon.

* * * * *